US005166341A

United States Patent [19]

Kon et al.

[11] Patent Number: 5,166,341

[45] Date of Patent: Nov. 24, 1992

[54] 6-AMINO-1,4-HEXAHYDRO-1H-DIAZEPINE DERIVATIVES

[75] Inventors: Tatsuya Kon, Ashiya; Shiro Kato, Sakai; Toshiya Morie, Matsubara; Tadahiko Karasawa, Toyonaka; Naoyuki Yoshida, Matsubara, all of Japan

[73] Assignee: Dainippon Pharmaceutical Co., Ltd., Osaka, Japan

[21] Appl. No.: 670,443

[22] Filed: Mar. 11, 1991

Related U.S. Application Data

[62] Division of Ser. No. 384,766, Jul. 25, 1989, Pat. No. 5,017,573.

[30] Foreign Application Priority Data

Jul. 29, 1988 [JP] Japan ................................ 63-191904
Dec. 20, 1988 [JP] Japan ................................ 63-322986

[51] Int. Cl.[5] .................... C07D 243/08; C07D 487/08

[52] U.S. Cl. .................................... 540/575; 540/472; 540/556

[58] Field of Search ......................... 540/556, 578, 472

[56] References Cited

U.S. PATENT DOCUMENTS 4,207,327 6/1980 Lunsford et al. .................. 424/273
4,474,964 10/1984 Ibuki et al. .......................... 546/199

FOREIGN PATENT DOCUMENTS 0067770 12/1982 European Pat. Off. .
0144986 6/1985 European Pat. Off. .
0200444 11/1986 European Pat. Off. .
0214772 3/1987 European Pat. Off. .
0230718 8/1987 European Pat. Off. .
0235878 9/1987 European Pat. Off. .
0247266 12/1987 European Pat. Off. .
0261964 3/1988 European Pat. Off. .
2648354 5/1977 Fed. Rep. of Germany .
52-83737 7/1977 Japan .
2125398 3/1984 United Kingdom .
2206788 1/1989 United Kingdom .

OTHER PUBLICATIONS

Gaertner, Journal of Heterocyclic Chemistry, vol. 18, No. 3, Jun., 1971, pp. 519-521.

Ungnade et al., Journal of Organic Chemistry, vol. 30, No. 2 (1965), pp. 354-359.

Bagga et al., Journal of The Chemical Society, Chemical Communications, (1987), pp. 259-261.

Beilsteins Handbuch der Organischen Chemie, 4th Edition 3rd and 4th Supplementary Series, vol. 25/3 (1981) p. 1982.

Saari et al., J. Org. Chem., vol. 36, No. 12, (1971), pp. 1711-1714.

Kon et al., Chemical Abstract vol. 112, No. 7473w (1989).

*Primary Examiner*—Cecilia Tsang
*Assistant Examiner*—Philip Datlow
*Attorney, Agent, or Firm*—Wenderoth, Lind & Ponack

[57] ABSTRACT

Indazole-3-carboxylic acid derivatives represented by the following general formula (I) and their physiologically acceptable acid addition salts or quaternary ammonium salts,

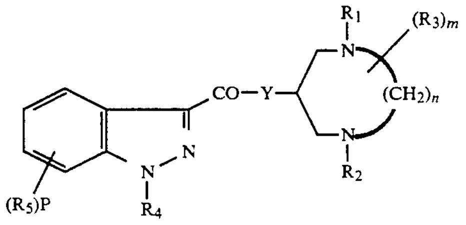

are useful as a potent and selective antagonist of serotonin 3 (5-$HT_3$) receptor. Also disclosed are compounds of the formula

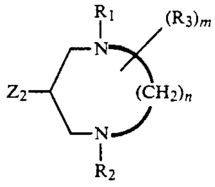

which are useful as intermediates in the production of the disclosed final product compounds.

16 Claims, No Drawings

6-AMINO-1,4-HEXAHYDRO-1H-DIAZEPINE DERIVATIVES

This application is a division of application Ser. No. 384,766, filed Jul. 25, 1989 (now U.S. Pat. No. 5,017,573).

This invention relates to a novel indazole-3-carboxylic acid derivative useful as a potent and selective antagonist of serotonin 3 (5-$HT_3$) receptor, processes for production thereof, a pharmaceutical composition comprising the above compound, and a novel intermediate for the above compound.

Since the development of 4-amino-5-chloro-N-[(2-diethylamino)ethyl]-2-methoxybenzamide [generic name: metoclopramide; see, for example, Merck Index, 10th edition, 6019 (1983)] in the mid-1960's as an antiemetic agent or a gastrointestinal motility enhancing agent, various substituted benzamide derivatives and heteroaromatic carboxamide derivatives have been synthesized and their pharmacological properties have been studied (for example, see Japanese Laid-Open Patent Publications Nos. 83737/1977 and 123485/1985, and U.S. Pat. No. 4,207,327).

On the other hand, since the discovery in the late 1970's of MDL-72222 (EP-A-67770) and ICS 205-930 (GB-A-2125398) which selectively antagonize serotonin M receptor (now the serotonin M receptor is classified as serotonin 3 receptor), some serotonin 3 receptor antagonists have been discovered (for example, see EP-A-200444, EP-A-235878 and EP-A-247266). It was reported that these compounds are effective not only for nausea and vomiting induced by anticancer agents, migraine and arrhythmia but also for schizophrenia, anxiety neurosis and dependence on alcohol, nicotine and narcotics (GB-A-2206788).

The present inventors made extensive investigations in order to find a novel potent and selective serotonin 3 (5-$HT_3$ antagonist), and have now found that indazole-3-carboxylic acid derivatives of the following general formula (I), and physiologically acceptable acid addition salts thereof and quaternary ammonium salts thereof have potent and selective 5-$HT_3$ receptor antagonizing activity.

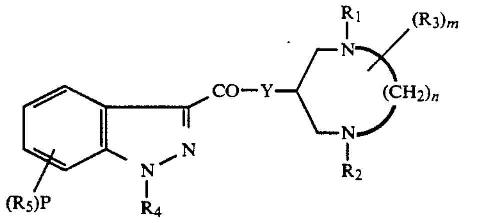
(I)

wherein

Y represents —NH— or —O—;

$R_1$ and $R_2$ are identical or different and each represents a hydrogen atom, a lower alkyl group, a substituted lower alkyl group, a cycloalkyl group, a lower alkenyl group, a cycloalkenyl group, a lower alkynyl group, an unsubstituted or substituted aryl-lower alkyl group, a lower alkoxycarbonyl group, an unsubstituted or substituted aralkyloxycarbonyl group or an acyl group, or $R_1$ and $R_2$, taken together, form a lower alkylene group;

$R_3$ represents a hydrogen atom, a lower alkyl group, or a phenyl group;

$R_4$ represents a hydrogen atom, a lower alkyl group, a substituted lower alkyl group, a cycloalkyl group, a lower alkenyl group, a cycloalkenyl group, a lower alkynyl group, an unsubstituted or substituted aryl-lower alkyl group, a lower alkoxycarbonyl group, an unsubstituted or substituted aralkyloxycarbonyl group or an acyl group;

$R_5$ represents a hydrogen atom, a halogen atom, a lower alkyl group, a lower alkoxy group, a hydroxyl group, a trifluoromethyl group, a nitro group, an amino group or an acylamino group;

m represents a number of 1, 2, 3 or 4;

n represents a number of 1, 2 or 3; and p represents a number of 1, 2, 3 or 4.

The term "lower", as used in the present specification and the appended claims, unless otherwise specified, means that a group or a compound qualified by this term has not more than 6, preferably not more than 4, carbon atoms.

The lower alkyl group, the lower alkenyl group, the lower alkynyl group and the lower alkylene group in this invention may be linear or branched. Specific examples of the lower alkyl group include methyl, ethyl, propyl, isopropyl, butyl, isobutyl, sec-butyl, tert-butyl, pentyl, isopentyl, neopentyl, tert-pentyl, hexyl and isohexyl. The lower alkenyl group may contain 1 or 2 double bonds, preferably one double bond. Specific examples of the lower alkenyl group include vinyl, propenyl, allyl, isopropenyl, butenyl. The lower alkynyl group may contain 1 or 2 triple bonds, usually only one triple bond, in the main chain, and its specific examples are propargyl, butan-3-ynyl, penten-4-ynyl and 2-penten-4-ynyl. The lower alkylene group includes, for example, methylene, trimethylene, propylene, tetramethylene, ethylethylene, pentamethylene and hexamethylene.

The lower alkoxy group and the lower alkoxycarbonyl group respectively mean a (lower alkyl)—O— group and a (lower alkyl)—O—CO— group in which the lower alkyl moiety has the above meaning. Specific examples of the lower alkoxy group are methoxy, ethoxy, propoxy, butoxy, isopropoxy, pentyloxy and hexyloxy.

Specific examples of the lower alkoxycarbonyl group include methoxycarbonyl, ethoxycarbonyl, propoxycarbonyl, isopropoxycarbonyl, butoxycarbonyl, pentyloxycarbonyl and hexyloxycarbonyl.

The cycloalkyl group includes saturated alicyclic groups having 3 to 8 carbon atoms. Specific examples are cyclopropyl, cyclobutyl, cyclopentyl, cyclohexyl, cycloheptyl, and cyclooctyl. The cycloalkenyl group is preferably an unsaturated alicyclic group having 5 to 8 carbon atoms and containing 1 or 2 double bonds, usually 1 double bond in its ring, and specific examples are 2-cyclopenten-1-yl, 2,4-cyclopentadien-1-yl, 1-cyclohexen-1-yl, 2-cyclohexen-1-yl, 3-cyclohexen-1-yl, 2-cyclohepten-1-yl and 2-cycloocten-1-yl, Examples of the halogen atom are fluorine, chlorine, bromine and iodine atoms.

The acyl moiety in the acyl group, the acylamino group and the acyloxy group is an organic carboxylic acid residue, and can specifically be a group represented by the following formula $$Q_1—CO—$$

wherein $Q_1$ represents a hydrogen atom, or an organic group, for example a saturated or unsaturated, chain or cyclic aliphatic hydrocarbon group, an aromatic or araliphatic group which may be substituted by, for example, halogen, lower alkyl, lower alkoxy, hydroxy, trifluoromethyl, cyano, amino or nitro, preferably a lower alkyl group, a lower alkenyl group or an unsubstituted or substituted aryl group. Specific examples of the acyl group include formyl, acetyl, propionyl, butyryl, isobutyryl, 2-methyl-2-phenoxyacetyl, acryloyl, methacryloyl, cinnamoyl, benzoyl, chlorobenzoyl, methylbenzoyl, methoxybenzoyl and nitrobenzoyl groups. In the substituted lower alkyl group, the substituent on the lower alkyl group may be, for example, a cycloalkyl group, a cycloalkenyl group, a lower alkoxy group, a hydroxyl group, a cyano group, an oxo group (=O), an acyloxy group, an unsubstituted or substituted amino group, a heterocyclic group having 1 or 2 hetero atoms selected from oxygen, nitrogen and sulfur atoms, or a halogen atom. The above lower alkyl may be substituted by at least one, for example 1 to 3, especially one, of these substituents. The unsubstituted or substituted amino group may include groups of the following formula

wherein $Q_2$ and $Q_3$ are identical or different, and each represents a hydrogen atom, a lower alkyl group, an unsubstituted or substituted aryl-lower alkyl group, or an acyl group, or $Q_2$ and $Q_3$, taken together with the nitrogen atom to which they are bonded, may form a heterocyclic group which may further include a hetero atom selected from nitrogen, oxygen and sulfur atoms. Specific examples of the above amino group include amino, methylamino, ethylamino, propylamino, isopropylamino, butylamino, tert-butylamino, dimethylamino, diethylamino, methylethylamino, methylpropylamino, benzylamino, (methoxybenzyl)amino, (nitrobenzyl)amino, methylbenzylamino, dibenzylamino, morpholino, 1-pyrrolidinyl, piperidino and 4-methyl-1-piperazinyl groups.

The heterocyclic group having 1 or 2 hetero atoms selected from oxygen, nitrogen and sulfur atoms may be heteroalicyclic or heteroaromatic. Examples of the heteroalicyclic group include tetrahydrofuryl, tetrahydrothienyl, tetrahydropyranyl, 2- or 3-pyrrolidinyl, 2-, 3- or 4-piperidinyl, 1,3-dioxolan-2-yl, 1,3- or 1,4-dioxocyclohexan-2-yl, 2- or 3-morpholinyl and 2-imidazolidinyl. The heteroaromatic group may be monocyclic or polycyclic (condensed cyclic), and its examples are furyl, thienyl, oxazolyl, isoxazolyl, pyridyl, indolyl, benzisoxazolyl, quinolyl and isoquinolyl groups.

Thus, specific examples of the substituted lower alkyl groups include 2-chloroethyl, 2-hydroxyethyl, 3-hydroxypropyl, 2-cyanoethyl, cyclopropylmethyl, 2-cyclopropylethyl, cyclohexylmethyl, 1-(cyclohexen-1-yl)methyl, 2-(1-cyclohexen-1-yl)ethyl, 2-methoxyethyl, 2-acetyloxyethyl, 3-aminopropoxy, 2-monoethylaminoethyl, 2-dimethylaminoethyl, 3-benzoylaminopropyl, tetrahydrofurylmethyl, 2-(2-tetrahydrofuryl)ethyl, 2-(3-tetrahydrofuryl)ethyl, 2-tetrahydrothiophenylmethyl, 2-tetrahydropyranylmethyl, 2-(1,3-dioxonyl)methyl, 2-(2-pyridyl)ethyl, 3-(1,3-dithioranyl)methyl, 2-, 3-, or 4-pyridylmethyl, 2- or 3-furylmethyl, 3-thiophenylmethyl, 3-benzisoxazolylmethyl and 2-quinolylmethyl.

The aryl in the unsubstituted or substituted aryl group may be monocyclic or polycyclic, and includes, for example, phenyl and naphthyl. The substituent on the aryl group may be, for example, a halogen atom, a lower alkyl group, a fluoromethyl group, a hydroxyl group, a lower alkoxy group, an unsubstituted or substituted amino group, a nitro group, a cyano group, a carboxyl group or a lower alkoxycarbonyl group. The aryl group may be substituted by 1 to 5, preferably 1 to 2, such substituents. Specific examples of the substituted aryl group include 2-, 3- or 4-methylphenyl, 2-, 3- or 4-fluorophenyl, 2,4-, 2,5-, or 3,5-difluorophenyl, 2,3,4,5,6pentafluorophenyl, 2-, 3- or 4-bromophenyl, 2-, 3- or 4-chlorophenyl, 2-, 3-, or 4-cyanophenyl, 3-fluoro-5-cyanophenyl, 2-, 3- or 4-methoxyphenyl, 2-, 3- or 4-nitrophenyl, 2-, 3- or 4-trifluoromethylphenyl, 2-, 3- or 4-aminophenyl, 2- 3- or 4-methoxycarbonylphenyl and 2-(1-methyl)naphthyl.

The unsubstituted or substituted aryl-lower alkyl group is a lower alkyl group substituted by the unsubstituted or substituted aryl group, in which the unsubstituted or substituted aryl moiety and the lower alkyl moiety in the unsubstituted or substituted aryl-lower alkyl group have the above-mentioned meanings. Specific examples of the unsubstituted or substituted aryl-lower alkyl group include 2-, 3- or 4-methylbenzyl, 2-, 3- or 4-fluorobenzyl, 2,4-, 2,5- or 3,5-difluorobenzyl, 2,3,4,5,6-pentafluorobenzyl, 2-, 3- or 4-bromobenzyl, 2-, 3- or 4-chlorobenzyl, 2-, 3- or 4-cyanobenzyl, 3-fluoro-5-cyanobenzyl, 2-, 3- or 4-nitrobenzyl, 2-, 3- or 4-trifluoromethylbenzyl, 2-, 3- or 4-aminobenzyl, 2-phenylethyl, 1-phenylethyl and 1-phenyl-1-methylethyl.

The unsubstituted or substituted aralkyloxycarbonyl group is an (unsubstituted or substituted aryl-lower alkyl)—O—CO— group, and includes, for example, benzyloxycarbonyl, 2-, 3- or 4-methylbenzyloxycarbonyl, 2-, 3- or 4-fluorobenzyloxycarbonyl, 2-, 3- or 4-bromobenzyloxycarbonyl, 2-, 3- or 4-chlorobenzyloxycarbonyl, 2-, 3- or 4-cyanobenzyloxycarbonyl, 2-, 3- or 4-trifluoromethylbenzyloxycarbonyl, 2-phenylethyloxycarbonyl and 1-phenylethyloxycarbonyl.

In general formula (I) above, Y is preferably —NH—, and n is preferably 2.

A preferred group of compounds of general formula (I) are those of general formula (I) in which $R_1$ represents a hydrogen atom or a lower alkyl group, $R_2$ represents a hydrogen atom; a lower alkyl group; a lower alkyl group substituted by $C_3$–$C_8$ cycloalkyl, $C_5$–$C_8$ cycloalkenyl, lower alkoxy, hydroxy, cyano, oxo, acyloxy, unsubstituted or substituted amino, a heterocyclic group having 1 to 2 hetero atoms selected from oxygen, nitrogen and sulfur atoms, or halogen; a $C_3$–$C_8$ cycloalkyl group; a lower alkenyl group; a $C_5$–$C_8$ cycloalkenyl group; an aryl-lower alkyl group which may optionally be substituted by halogen, lower alkyl, trifluoromethyl, hydroxy, lower alkoxy, unsubstituted or substituted amino, nitro, cyano, carboxy, or lower alkoxycarbonyl; a lower alkoxycarbonyl group; an aralkyloxycarbonyl group; or an acyl group, or $R_1$ and $R_2$, taken together, represents a lower alkylene group, $R_3$ represents a hydrogen atom, a lower alkyl group or a phenyl group, $R_4$ represents a hydrogen atom; a lower alkyl group; a lower alkyl group substituted by $C_3$–$C_8$ cycloalkyl, $C_5$–$C_8$ cycloalkenyl, lower alkoxy, hydroxy, cyano, oxo, acyloxy, substituted or unsubstituted amino, a heterocyclic group having 1 to 2 hetero atoms selected oxygen, nitrogen and sulfur, or halogen; a $C_3$–$C_8$ cycloalkyl group; a lower alkenyl group; a $C_5$–$C_8$ cycloalkenyl group; an aryl-lower alkyl group which may optionally be substituted by halogen, lower alkyl, trifluoromethyl, hydroxy, lower alkoxy, unsubstituted or substituted amino, nitro, cyano, carboxy or lower alkoxycarbonyl; a lower alkoxycarbonyl group; an aralkyloxycarbonyl group; or an acyl group, $R_5$ represents a hydrogen atom, a halogen atom, a lower alkyl group, a hydroxyl group, a lower alkoxy group or a trifluoromethyl group, m is 1, and p is 1 or 2.

A more preferred group of the compounds of formula (I) provided by this invention are compounds of the following general formula (I-1)

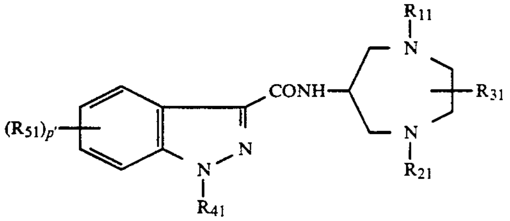
(I-1)

wherein $R_{11}$ represents a hydrogen atom or a lower alkyl group, $R_{21}$ represents a hydrogen atom; a lower alkyl group; a lower alkyl group substitutted by $C_3$–$C_6$ cycloalkyl, $C_5$–$C_6$ cycloalkenyl, or a 5- to 6-membered heterocyclic group having 1 to 2 hetero atoms selected from oxygen and nitrogen atoms; a $C_3$–$C_6$ cycloalkyl group; an allyl group; or a phenyl-lower alkyl group which may optionally be substituted by halogen, lower alkyl, trifluoromethyl, lower alkoxy, nitro or cyano, $R_{31}$ represents a hydrogen atom or a lower alkyl group, $R_{41}$ represents a hydrogen atom; a lower alkyl group; a lower alkyl group substituted by $C_3$–$C_6$ cycloalkyl, $C_5$–$C_6$ cycloalkenyl, lower alkoxy, hydroxy or oxo; a $C_3$–$C_6$ cycloalkyl group; an allyl group; an aryl-lower alkyl group which may optionally be substituted by halogen, lower alkyl, trifluoromethyl, hydroxy, lower alkoxy, unsubstituted or substituted amino, nitro, cyano, carboxy or lower alkoxycarbonyl; a lower alkoxycarbonyl group; a lower alkanoyl group; or a benzoyl group, $R_{51}$ represents a hydrogen atom, a halogen atom, a lower alkyl group or a hydroxyl group, and p' is 1 or 2.

An especially preferred group of the compounds of this invention are those of formula (I-2) below

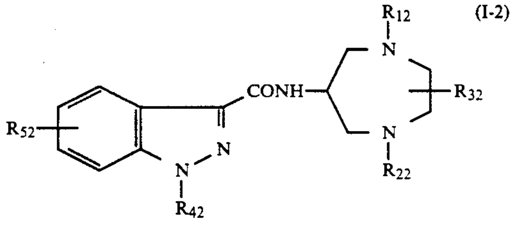
(I-2)

wherein $R_{12}$ represents an alkyl group having 1 to 4 carbon atoms, $R_{22}$ represents a hydrogen atom; a $C_1$–$C_4$ alkyl group; a pyridylmethyl group; or a benzyl group which may optionally be mono- or di-substituted by halogen, $C_1$–$C_4$ alkyl, trifluoromethyl, $C_1$–$C_4$ alkoxy or cyano, $R_{32}$ represents a hydrogen atom or an alkyl group having 1 to 4 carbon atoms, $R_{42}$ represents a hydrogen atom, a $C_1$–$C_4$ alkyl group, a hydroxyethyl group, a 2-butanon-3-yl group, a cyclopropylmethyl group, an allyl group, a $C_5$–$C_6$ cycloalkyl group, a benzyl group, a $C_2$–$C_4$ alkoxycarbonyl group, a $C_2$–$C_4$ alkanoyl group, or a benzoyl group, and $R_{52}$ represents a hydrogen atom or a halogen atom.

It is especially preferred that in formula (I-2), $R_{12}$ represent a methyl or ethyl group, $R_{22}$ represent a methyl group, an ethyl group, a benzyl group, a methylbenzyl group, a fluorobenzyl group, a chlorobenzyl group, a bromobenzyl group, a trifluoromethylbenzyl group, a methoxybenzyl group, a cyanobenzyl group, a difluorobenzyl group, a dimethylbenzyl group or a pyridylmethyl group, $R_{32}$ represent a hydrogen atom or a methyl group, $R_{42}$ represent a hydrogen atom, a methyl group, an ethyl group, a propyl group, a butyl group, a hydoxyethyl group, a allyl group, a cyclopropylmethyl group, a cyclopentyl group, a benzyl group, an acetyl group, a propionyl group, a benzoyl group, a 2-butanon-3-yl group, a methoxycarbonyl group, or an ethoxycarbonyl group, and $R_{52}$ represents a hydrogen atom, a chlorine atom or a fluorine atom.

Specific examples of the compounds of this invention are given below.

N-[1-(3-methylbenzyl)-4-methylhexahydro-1H-1,4-diazepin-6-yl]-1-indazole-3-carboxamide, N-[1-(4-methylbenzyl)-4-methylhexahydro-1H-1,4-diazepin-6-yl]-1H-indazole-3-carboxamide, N-[1-(3-pyridylmethyl)-4-methylhexahydro-1H-1,4-diazepin-6-yl]-1H-indazole-3-carboxamide, N-[1-(4-pyridylmethyl)-4-methylhexahydro-1H-1,4-diazepin-6-yl]-1H-indazole-3-carboxamide, N-[1-(3-fluorobenzyl)-4-methylhexahydro-1H-1,4-diazepin-6-yl]-1H-indazole-3-carboxamide, N-[1-(4-fluorobenzyl)-4-methylhexahydro-1H-1,4-diazepin-6-yl]-1H-indazole-3-carboxamide, N-[1-(2-cyanobenzyl)-4-methylhexahydro-1H-1,4-diazepin-6-yl]-1H-indazole-3-carboxamide, N-[1-(4-cyanobenzyl)-4-methylhexahydro-1H-1,4-diazepin-6-yl]-1H-indazole-3-carboxamide, N-[1-(4-bromobenzyl)-4-methylhexahydro-1H-1,4-diazepin-6-yl]-1H-indazole-3-carboxamide, N-[1-(3,5-difluorobenzyl)-4-methylhexahydro-1H-1,4-diazepin-6-yl]-1H-indazole-3-carboxamide, N-(1-benzyl-2,4-dimethylhexahydro-1H-1,4-diazepin-6-yl)-1H-indazole-3-carboxamide, N-(1-benzyl-4-methylhexahydro-1H-1,4-diazepin-6-yl)-1-methyl-1H-indazole-3-carboxamide, N-(1-benzyl-4-methylhexahydro-1H-1,4-diazepin-6-yl)-1-acetyl-1H-indazole-3-carboxamide, N-(1-benzyl-4-methylhexahydro-1H-1,4-diazepin-6-yl)-1-propionyl-1H-indazole-3-carboxamide, N-[1-(3-fluoro-5-cyanobenzyl)-4-methylhexahydro-1H-1,4-diazepin-6-yl]-1H-indazole-3-carboxamide, N-[1-(3,4-dibromobenzyl)-4-methylhexahydro-1H-1,4-diazepin-6-yl]-1H-indazole-3-carboxamide, N-[1-(3-fluorobenzyl)-4-methylhexahydro-1H-1,4-diazepin-6-yl]-1-isobutyl-1H-indazole-3-carboxamide,
N-[1-(2-cyanobenzyl)-4-methylhexahydro-1H-1,4-diazepin-6-yl]-1-formyl-1H-indazole-3-carboxamide,
N-[1-(4-chlorobenzyl)-4-methylhexahydro-1H-1,4-diazepin-6-yl]-1-(2-propyonyl)-1H-indazole-3-carboxamide,
N-(1-furfuryl-4-methylhexahydro-1H-1,4-diazepin-6-yl)-1H-indazole-3-carboxamide,
N-(1-thenyl-4-methylhexahydro-1H-1,4-diazepin-6-yl)-1H-indazole-3-carboxamide,
N-[1-(2-tetrahydrofurylmethyl)-4-methylhexahydro-1H-1,4-diazepin-6-yl]-1H-indazole-3-carboxamide,
N-(1-benzyl-4-ethylhexahydro-1H-1,4-diazepin-6-yl)-1H-indazole-3-carboxamide, and
(1-benzyl-4-methylhexahydro-1H-1,4-diazepin-6-yl) 1H-indazole-3-carboxylate.

The compounds of formula (I) provided by this invention can exist in the form of an acid addition salt or a quaternary ammonium salt. For example they may be inorganic acid salts such as hydrochlorides, hydrobromides, hydroiodides, sulfates and phosphates, or organic acid salts such as oxalates, maleates, fumarates malonates lactates, malates, citrates, tartrates, benzoates and methanesufonates. Examples of quatenary ammonium salts of the compounds of formula (I) are quaternary ammonium salts with lower alkyl halides such as methyl iodides, methylbromides, ethyliodides and ethylbromides, lower alkyl lower alkylsufonates such as methyl methanesulfonate and ethyl methanesulfonate, and lower alkyl arylsulfonates such as methyl p-toluenesulfonates. Of these, physiologically acceptable salts are preferred.

The comounds (I) of this invention may be produced by the following processes.

Process (a)

In one aspect, the compound (I) of this invention can be produced by reacting a compound of the following general

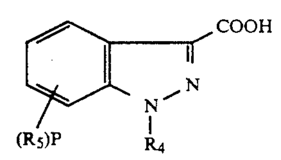

(II)

wherein $R_4$, $R_5$ and p are as defined, or its reactive derivative with a compound of the following general formula (III)

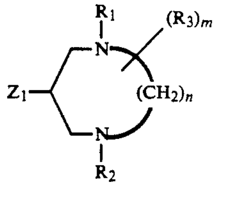

(III)

wherein $Z_1$ is $-NH_2$ or $-OH$, and $R_1$, $R_2$, $R_3$, n and m are as defined hereinabove, or its reactive derivative.

The reactive derivative of the compound of formula (II) may be, for example, a lower alkyl ester, an activated ester, an acid anhydride, an acid halide (particularly an acid chloride) and a dimer of the compound of formula (II) [see, for example, J. Org. Chem., 23,621 (1958)]. Specific examples of the activated ester include a p-nitrophenyl ester, a 2,4,5-trichlorophenyl ester, a pentachlorophenyl ester, a cyanomethyl ester, an N-hydroxysuccinimide ester, an N-hydroxyphthalimide ester, a 1-hydroxybenzotriazole ester, an N-hydroxy-5-norbornene 2,3-dicarboximide ester, an N-hydroxypiperidine ester, an 8-hydroxyquinoline ester, a 2-hydroxyphenyl ester, a 2-hydroxy-4,5-dichlorophenyl ester, a 2-hydroxypyridine ester and a 2-pyridylthiol ester. A symmetric mixed acid anhydride or a mixed acid anhydride may be used as the acid anhydride. Specific examples of the mixed acid anhydride are mixed acid anhydrides with alkyl chloroformates such as ethyl chloroformate and isobutyl chloroformate, mixed acid anhydrides with aralkyl chloroformates such as benzyl chloroformate, mixed acid anhydrides with aryl chloroformates such as phenyl chloroformate, and mixed acid anhydrides with alkanoic acids such as isovaleric acid and pivalic acid.

When the compound of formula (II) itself is used as the starting material, the reaction may be carried out in the presence of a condensing agent such as dicyclohexyl carbodiimide, 1-ethyl-3-(3-dimethylaminopropyl)carbodiimide hydrochloride, N,N'-carbonyldiimidazole, N,N'-carbonyldisuccinimide, 1-ethoxycarbonyl-2-ethoxy-1,2-dihydroquinoline and diphenylphosphoryl azide.

Examples of the reactive derivative of a compound of formula (III) in which $Z_1$ is $-OH$ are lithium salts or sodium salts of compounds of formula (III) in which $Z_1$ is $-OH$ in the presence of strong bases such as n-butyl lithium, lithium isopropylamine, or sodum hydride.

The reaction of the compound (II) or its reactive derivative with the compound (III) or its reactive derivative is carried out in a solvent or in the absence of solvent. The solvent used should be properly selected according to the types of the starting materials, for example. Examples of the solvent include aromatic hydrocarbons such as benzene, toluene and xylene, ethers such as diethyl ether, tetrahydrofuran and dioxane, halogenated hydrocarbons such as methylene chloride and chloroform, alcohols such as ethanol and isopropanol, ethyl acetate, acetone, acetonitrile, N,N-dimethylformamide, dimethyl sulfoxide, ethylene glycol and water. These solvents may be used singly or in combination with each other. This reaction is carried out, as required, in the presence of a base. Specific examples of the base are alkali hydroxides such as sodium hydroxide and potassium hydroxide, alkali bicarbonates such as sodium bicarbonate and potassium bicarbonate, alkali carbonates such as sodium carbonate and potassium carbonate, and organic bases such as triethylamine, tributylamine, diisopropylethylamine and N-methylmorpholine. The compound (III) in which $Z_1$ is $-NH_2$ may be used in an excessive amount to cause it serve concurrently as the base. The proportion of the compound (III) used with respect to the compound (II) is not particularly limited. Generally, it is preferred to use the compound (III) in an amount of 1 to 3 moles, especially 1 to 1.5 moles, per mole of the compound (II).

The reaction temperature varies with the types of the starting materials used. Usually, it may be $-30°$ C. to about 200° C., preferably about $-10°$ C. to about 150° C. If the compound (II), its reactive derivative, the compound (III), or its reactive derivative has in its structure functional groups, it is desirable to protect them in a customary manner and eliminate the protecting groups after the reaction.

Process (b)

Compounds of formula (I) in which $R_4$ is as defined excepting hydrogen may also be produced by reacting a compound of general formula (I-3)

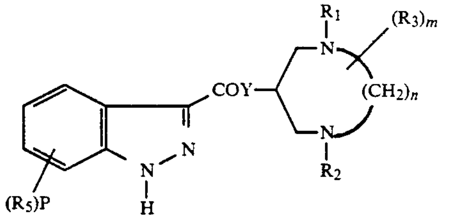
(I-3)

wherein $R_1$, $R_2$, $R_3$, $R_5$, Y, m, n and p, with a compound of the formula (IV)

$X_1—R_{43}$ (IV)

wherein $X_1$ represents a residue of a reactive ester of an alcohol, and $R_{43}$ represents the groups defined for $R_4$ above except hydrogen.

The residue of the reactive ester of an alcohol represented by $X_1$ in formula (IV) may be, for example, a halogen atom such as a chlorine, bromine or iodine atom, a lower alkylsulfonyloxy group such as methansulfonyloxy and ethanesulfonyloxy, or an arylsulfonyloxy group such as benzenesulfonyloxy and p-toluenesulfonyloxy. Where $R_{43}$ is an acyl group, an acid anhydride of a carboxylic acid corresponding to $R_{43}$ may be used as compound (IV).

The reaction of the compound (I-3) with the compound (IV) is carried out usually in an appropriate solvent. Specific examples of the solvent include aromatic hydrocarbons such as benzene, toluene and xylene, ketones such as acetone and methyl ethyl ketone, ethers such as tetrahydrofuran and dioxane, alcohols such as ethanol and isopropyl alcohol, acetonitrile, chloroform, ethyl acetate, N,N-dimethylformamide and dimethyl sulfoxide. These solvents may be used singly or in combination with each other. Desirably, this reaction is carried out in the presence of a base. Specific examples of the base may be the same as those described above with regard to process (a). When a compound of formula (IV) in which $X_1$ is chlorine or bromine is used, the addition of an alkali metal iodide such as sodium iodide or potassium iodide enables the reaction to proceed smoothly.

The proportion of the compound of formula (IV) used relative to the compound of formula (I-3) is not critical, and can be varied over a broad range. Generally, it is convenient to use the compound of formula (IV) in an amount of 1 to 5 moles, especially 1 to 2 mole, per mole of the compound of formula (I-3). The reaction temperature, which varies with the types of the starting materials, for example, is usually about 50° to about 200° C. If the compound (I-3) or the compound (IV) has functional groups, it is desirable to protect them in a customary manner and eliminate the protecting groups after the reaction.

Process (c)

Compounds of formula (I) in which $R_1$ and $R_2$ are as defined above excepting hydrogen may also be produced by reacting a compound of the general formula (I-4)

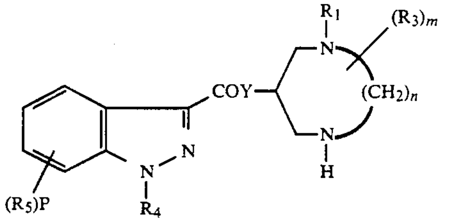
(I-4)

wherein $R_1$, $R_3$, $R_4$, $R_5$, Y, m, n and p are as defined above, with a compound of the following formula (V)

$X_2—R_{23}$ (V)

wherein $X_2$ represents the same reactive ester residue as mentioned with regard to $X_1$, and $R_{23}$ represents the groups defined for $R_2$ excepting hydrogen.

Usually, the reaction between the compound of formula (I-4) and the compound of formula (V) may be carried out by using the same method and conditons as described above with regard to process (b). If $R_{23}$ in formula (V) is an acyl group, an acid anhydride of a carboxylic acid corresponding to $R_{23}$ may also be used as the compound (V). When the compound of formula (I-4) or the compound of formula (V) has functional groups, it is desirable to protect them in a customary manner and eliminate the protecting groups after the reaction.

Process (d)

Compounds of formula (I) in which either one of $R_1$ and $R_2$ is a hydrogen atom or both $R_1$ and $R_2$ are hydrogen atoms may also be produced by catalytically reducing a compound represented by the general formula (I-5)

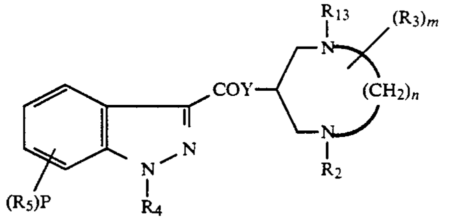
(I-5)

wherein $R_{13}$ represents an unsubstituted or substituted benzyl group, and $R_2$, $R_3$, $R_4$, $R_5$, Y, m, n and p are as defined above, in the presence of a catalyst such as palladium-carbon, Raney-nickel or platinum oxide in accordance with a method known per se, for example in a solvent.

The solvent may be those which are usually employed in catalytic reduction, such as alcohols (e.g., ethanol and methanol), water, and acetic acid. The reaction temperature is usually 0° to 80° C. When the compound of formula (I-5) has functional groups, it is desirable to protect them in a customary manner and eliminate the protecting groups after the reaction.

The compounds of formula (I) obtained by any of these processes may be isolated and purified by methods known per se, for example, chromatography, recrystallization, and reprecipitation.

Depending upon the selection of the starting compounds, the reaction and treating conditions, etc., the compound of formula (I) may be obtained in the form of a free base or an acid addition salt. The acid addition salt may be converted to a free base by a conventional method, for example, by treating it with a base such as an alkali carbonate or an alkali hydroxide. The free base, on the other hand, may be converted to an acid addition salt by treatment with an acid in accordance with a conventional method.

The quaternary ammonium salt of the compound of formula (I) may be produced by reacting the compound (I) with a compound composed of an alkyl group or a benzyl group and an anionic component such as a halogenide, a lower alkyl sulfate, a lower alkyl sulfonate, a substituted or unsubstituted benzenesulfonate or a nitrate (e.g., methyl iodide or benzyl bromide).

This reaction may be carried out by conventional methods in the production of quaternary ammonium salts, and the two compounds are reacted in a solvent or in the absence of solvent. Specific examples of the solvent include aromatic hydrocarbons such as benzene, toluene and xylene, ethers such as tetrahydrofuran and dioxane, dialkyl ketones such as acetone, methyl ethyl ketone and methyl isobutyl ketone, lower alcohols such as methanol, ethanol and isopropyl alcohol, acetonitrile, N,N-dimethylformamide, and mixtures of these. The reaction temperature, which may vary with the types of the starting materials and the reaction solvent, are usually about 10° to about 130° C., and the reaction time may usually be 10 minutes to 72 hours.

The compounds of formula (III) used as the starting material in process (a) and their precursors of the following formula (III')

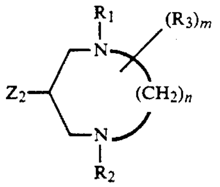

(III')

wherein $R_1$, $R_2$, $R_3$, m and n are as defined above; and $Z_2$ represents $-NR_6R_7$ or $-OR_6$ in which $R_6$ represents a hydrogen atom, a lower alkoxycarbonyl group, an unsubstituted or substituted aralkyloxycarbonyl group or an acyl group, and $R_7$ represents a hydrogen atom, a lower alkoxycarbonyl group, an unsubstituted or substituted aralkyloxycarbonyl group, an acyl group, a lower alkylsulfonyl group, an unsubstituted or substituted arylsulfonyl group or a trityl group, or $R_6$ and $R_7$, taken together with the nitrogen atom to which they are bonded, may represent a phthalimide group; provided that $R_1$ and $R_2$ do not simultaneously represent a benzyl group, are novel compounds not described in the prior literature, and can be produced by the following processes.

Compounds of formula (III') in which $R_6$ and $R_7$ are as defined above excepting hydrogen can be converted to compounds (III) in which $R_6$ and $R_7$ are hydrogen atoms usually by hydrolysis with acids or alkalies, catalytic reduction or reaction with hydrazine although the method should be properly selected depending upon the type of the compounds of formula (III').

Examples of the compounds of formula (III') in which $R_6$ and $R_7$ are other than hydrogen are 6-acetylamino-1-benzyl-4-methylhexahydro-1H-1,4-diazepine,
6-acetylamino-1-(3-methylbenzyl)-4-methylhexahydro-1H-1,4-diazepine,
6-acetylamino-1-(3-fluorobenzyl)-4-methylhexahydro-1H-1,4-diazepine,
6-acetylamino-1-(4-cyanobenzyl)-4-methylhexahydro-1H-1,4-diazepine,
6-acetylamino-1-(3-cyanobenzyl)-4-propylhexahydro-1H-1,4-diazepine,
6-acetylamino-1-(3,5-difluorobenzyl)-4-methylhexahydro-1H-1,4-diazepine,
6-acetylamino-1-(3-pyridylmethyl)-4-methylhexahydro-1H-1,4-diazepine,
6-acetylamino-1,4-dimethylhexahydro-1H-1,4-6-acetylamino-1,4-diethylhexahydro-1H-1,4-diazepine,
6-acetylamino-1,4-diethylhexahydro-1H-1,4-diazepine,
6-benzenesulfonylamino-1-benzyl-2,4-dimethylhexahydro-1H-1,4-diazepine,
6-benzyloxycarbonylamino-1-(3-methylbenzyl)-4-methylhexahydro-1H-1,4-diazepine,
6-ethoxycarbonylamino-1-benzyl-4-methylhexahydro-1H-1,4-diazepine,
6-(4-methylphenyl)sulfonylamino-1,4-dimethylhexahydro-1H-1,4-diazepine, and
N-(1-benzyl-4-methylhexahydro-1H-1,4-diazepin-6-yl)phthalimide.

Since the compounds of formulae (I) and (III) have at least one asymmetric carbon atom, their stereoisomers, mixtures thereof and racemic mixtures are embraced within the compounds of this invention. The compounds (I) may exist as hydrates and solvates which are also included within the compounds of this invention.

Process (1)

The compounds of formula (III') of this invention can be produced by reacting a compound of the general formula (VI)

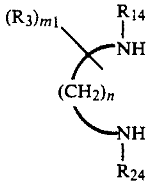

(VI)

wherein $m_1$ represents 1 or 2, $R_{14}$ and $R_{24}$ represent the groups defined above for $R_1$ and $R_2$ excepting hydrogen, and $R_3$ and n are as defined above, or its reactive derivative with a compound represented by the general formula (VII)

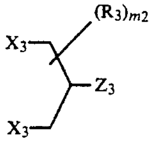

(VII)

wherein $X_3$ represents the same reactive ester residue as described above for $X_1$, $Z_3$ represents the same groups defined above for $Z_2$ excepting $-NH_2$, $R_3$ and m are as defined above, $m_2$ represents 1 or 2 and $m_1+m_2=m$, or its reactive equivalent of the following general formula (VIIIa) or (VIIIb)

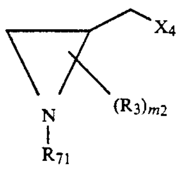 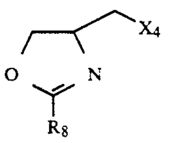

(VIIIa) (VIIIb)

wherein $R_8$ represents an aryl group, $X_4$ represents the same reactive ester residue as described above with regard to $X_1$, $R_{71}$ represents the same groups defined above for $R_7$ other than hydrogen, $m_2$ represents 1 or 2, the sum of $m_1 + m_2$ is 1, 2, 3 or 4, and $R_3$ is as defined above.

The reactive derivative of the compound of formula (VI) may be, for example, a lithium or sodium salt of the compound of formula (VI) in the presence of a strong base such as n-butyllithium, lithiunisopropylamine or sodium hydride.

The reaction of the compound (VI) with the compound (VII), (VIIIa) of (VIIIb) is usually carried out in an appropriate solvent. Specific examples of the solvent include aromatic hydrocarbons such as benzene, toluene and xylene, ketones such as acetone and methyl ethyl ketone, ethers such as tetrahydrofuran and dioxane, alcohols such as ethanol and isopropanol, acetonitrile, chloroform, ethyl acetate, N,N-dimethylformamide, dimethyl sulfoxide and water. These solvents may be used singly or in combination with each other. This reaction is preferably carried out in the presence of a base. Specific examples of the base may be the same as those given above with regard to process (a). When a compound of formula (VII), (VIIIa) or (VIIIb) in which $X_3$ and $X_4$ are chlorine or bromine is used, the addition of an alkali metal iodide such as sodium iodide or potassium iodide enables the reaction to proceed smoothly.

The proportion of the compound (VII), (VIIIa) or (VIIIb) relative to the compound (VI) is not particularly critical, and may be varied over a broad range. Generally, it is convenient to use the compound (VII), (VIIIa) or (VIIIb) in an amount of 1 to 5 moles, especially 1 to 2 moles, per mole of the compound of formula (VI). The reaction temperature, which differs depending upon the starting materials used, is usually about 10° to about 200° C. If the compound (VI), (VII), (VIIIa) or (VIIIb) has functional groups in its structure, it is desirable to protect these groups in a customary manner, and eliminate the protecting groups after the reaction.

Process (2)

Compounds of formula (III') in which $Z_2$ is $-NH_2$ can be produced by reacting a compound represented by the general formula (IX)

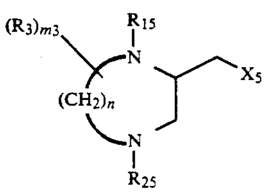

(IX)

wherein $m_3$ is 1, 2 or 3, $R_{15}$ and $R_{25}$ represent the same groups defined above for $R_1$ and $R_2$ excepting hydrogen, $X_5$ represents the same reactive ester residue as defined above for $X_1$, and $R_3$ is as defined, provided that $R_3$ is not bonded to the carbon to which $-CH_2X_5$ is bonded, with a nucleophilic agent such as sodium azide or potasium phthalimide, and thereafter, if sodium azide is used as the nucleophilic agent, catalytically reducing the resulting product using a catalyst such as palladium-carbon, Raney-nickel or platinum oxide or reducing the product using a reducing agent such as lithium aluminum hydride or bis(2-methoxyethoxy)aluminum hydride, and if potassium phthalimide is used as the nucleophilic agent, hydrolyzing the product with an acid or treaing it with hydrazine.

The reaction of the compound of formula (IX) with sodium azide or potassium phthalimide is carried out usually in an appropriate solvent. Specific examples of the solvent include aromatic hydrocarbons such as benzene, toluene and xylene, ketones such as acetone and methyl ethylketone, ethers such as tetrahydrofuran and dioxane, alcohols such as ethanol and isopropanol, acetonitrile, chloroform, ethyl acetate, N,N-dimethylformamide and dimethyl sulfoxide. These solvents may be used singly or in combination with each other.

The proportion of sodium azide or potassium phthalimide relative to the compound of formula (IX) is not critical in particular, and can be varied over a broad range. Generally, it is convenient to use 1 to 5 moles, particularly 1 to 3 moles, of sodium azide or potassum phthalimide, per mole of the compound of formula (IX). The reaction temperature, which varies with the types of the starting materials, is usually about 50° C. to about 200° C.

The catalytic reduction may be carried out in a solvent usually employed in catalytic reduction, for example an alcohol (e.g., ethanol or methanol), water and acetic acid. Toluene and ethers such as diethyl ether and tetrahydrofuran may be used in the reaction with a reducing agent such as lithium aluminum hydride. These reducing reactions may usually be carried out at 0° to 80° C.

The acid hydrolysis is carried out by using an inorganic acid such as hydrochloric acid and sulfuric acid. For example, alcohols (e.g., methanol or ethanol), water, N,N-dimethylformamide and dimethyl sulfoxide may be used as a solvent. The reaction with hydrazine is carried out by usually employing an alcohol such as methanol or ethanol as a solvent. These reactions are carried out usually at 30° to 150° C.

When the compounds to be reacted have functional groups which may participate in the reaction, it is necessary to choose a reaction in which these groups are not involved.

Process (3)

Compounds of formula (III') in which $Z_2$ is $-NH_2$ can be produced by reacting a compound represented by the general formula (X)

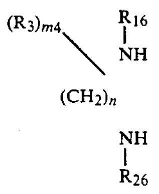

(X)

wherein $m_4$ is 1 or 2, $R_{16}$ and $R_{26}$ represent the groups defined above for $R_1$ and $R_2$ excepting hydrogen, and $R_3$ and n are as defined above, with formalin and nitromethane, or tris(hydroxymethyl)nitromethane, their equivalent to give a compound represented by the general formula (XI)

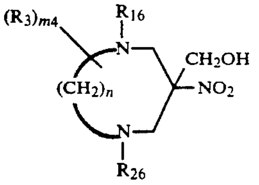

(XI)

wherein $m_4$, n, $R_{16}$, $R_{26}$ and $R_3$ are as defined above, eliminating the formalin by the action of a base, and reducing the resulting compound of general formula (XII)

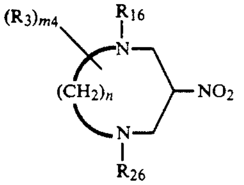

(XII)

wherein $m_4$, n, $R_{16}$, $R_{26}$ and $R_3$ are as defined above.

The reaction of the compound of formula (X) with formalin and nitromethane, or tris(hydroxymethyl)nitromethane is usually carried out in an appropriate solvent. Specific examples of the solvent include ketones such as acetone and methyl ethyl ketone, ethers such as tetrahydrofuran and dioxane, alcohols such as ethanol and isopropanol, acetonitrile, chloroform, ethyl acetate, N,N-dimethylformamide, dimethyl sulfoxide and water. These solvents are used singly or in combination with each other. This reaction is preferably carried out in the presence of a base. Specific examples of the base may be the same as given above with regard to process (a).

The proportion of formalin and, nitromethane, or tris(hydroxymethyl)nitromethane relative to the compound of formula (X) is not particularly limited, and may be varied over a broad range. Generally, it is convenient to use 1 to 5 moles of nitromethane, 2 to 8 moles of formalin and 1 to 5 moles of tris(hydroxymethyl)nitromethane, particualrly 1 to 2 moles of nitromethane, 2 to 3 moles of formalin and 1 to 2 moles of tris(hydroxymethyl)nitromethane, per mole of the compound of formula (X). The reaction temperature, which differs depending upon the types of the starting materials, is usually about 10° to about 200° C.

The base used in the reaction of the compound of formula (XI) may be a strong base such as a sodium alkoxide, potassium tert-butoxide or sodium hydride. The reaction is carried out in an appropriate solvent. Specific examples of the solvent include aromatic hydrocarbons such as benzene, toluene and xylene, ethers such as tetrahydrofuran and dioxane, alcohols such as ethanol and isopropanol, acetonitrile, chloroform, ethyl acetate, N,N-dimethylformamide and dimethyl sulfoxide. These solvents are used singly or in combination with each other.

The proportion of the strong base used relative to the compound of formula (XI) is not particularly limited, and can be varied over a broad range. Generally, it is convenient to use 1 to 5 moles, especially 1 to 2 moles, of the base, per mole of the compound of formula (X). The reaction temperature differs depending upon the types of the starting materials. Usually, it is about 20 ° C. to about 100° C.

The catalytic reduction of the compound of formula (XII) and the reduction with a metal may be carried out in a customary manner. Solvents used in ordinary catalytic reduction, such as alcohols, (e.g., ethanol or methanol), water and acetic acid, may be used in the catalytic reduction. The reaction temperature differs with the types of the staring materials used, and is usually about 0° C. to about 80° C. If the compounds of formula (X), (XI) or (XII) has functional groups, it is desirable to protect them in a customary manner and eliminate the protecting groups after the reaction.

Process (4)

Compounds of formula (III') in which one or both of $R_1$ and $R_2$ are hydrogen atoms can be produced by catalytically reducing a compound represented by the following formula (III'')

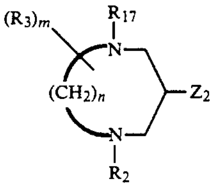

(III'')

wherein $R_{17}$ represents an unsubstituted or substituted benzyl group, and $R_2$, $Z_2$, m and n are as defined above, in the presence of a catalyst such as palladium-carbon, Raney-nickel or platinum oxide by an ordinary method.

Solvents usally employed in catalytic reduction, such as alcohols (e.g., ethanol or methanol), water and acetic acid may be used in this catalytic reduction. The reaction temperature is usually 0° to 80° C. If the compound of formula (III'') has functional groups in its structure, it is desirable to protect them in a customary manner and eliminate the protecting groups after the reaction.

The compounds of formula (I) provided by this invention have potent and selective serotonin 3 ($5\text{-}HT_3$) receptor antagonizing activity, and the pharmacological activities of typical examples of the compounds of formula (I) can be demonstrated by the following in vitro and in vivo tests.

TEST 1

Effect on Von Bezold-Jarisch reflex in rats (Serotonin 3 receptor antagonist activity)

The test was carried out substantially by the method of Fozard et al. [cf. Arch. Pharmacology, 326, 36–44 (1984)]. Male Wistar rats weighing 250–350 g or male SD rats weighing 300–400 g were anesthetized with urethane (1.5 g/kg, interraperitoneal) and placed on their back. An electrocardiogram (lead II) and a heart rate on the animals were recorded on an inkwriting oscillograph via a biophysical amplifier and a pulse rate tachomether, respectively. When 2-methylserotonin ($5\text{-}HT_3$ agonist) at 10–30 μg/kg was administered intravenously, the heart rate was transiently decreased (Von Bezold-Jarisch reflex). After stable responses were obtained following repeated administration of 2-methylserotonin at 15-minute intervals, the test compound (1 μg/kg) was administered intravenously 3 minutes before administration of 2-methylserotonin. The inhibition rate of the test compound was calculated as follows.

$$\text{Inhibition rate (\%)} = \left(1 - \frac{\text{Value after test compound}}{\text{Value before test compound}}\right) \times 100$$

Inhibition rate are shown in Table 1.

TABLE 1

| Effect on Von Bezold-Jarisch reflex in rats | | | |
|---|---|---|---|
| Test compound | Inhibition rate (%) | Test compound | Inhibition rate (%) |
| 1(a)* | 82 | 16 | 85 |
| 1(b) | 83 | 17 | 91 |
| 3 | 92 | 23 | 86 |
| 5 | 78 | 33 | 96 |
| 6 | 75 | 46 | 70 |
| 7 | 84 | 48 | 79 |
| 8 | 77 | 52 | 89 |
| 10 | 82 | 53 | 83 |
| 11 | 95 | 67 | 72 |
| 13 | 83 | 69 | 90 |

*)Compound of Example 1 (a) (herinafter, the same)

TEST 2

Effect on cisplatin-induced vomiting in ferrets and acute toxicity in mice

Male ferrets (Marshall Lab., U.S.A.) weighing approximately 1 kg were used. For intravenous injection, a cannule was implanted in the cervical vein under pentobarbital anethesia. The experiments were started 3 and 4 days after the operation. Saline (2 ml/kg) as a control group and a dose (0.03 mg/kg) of a test compound as a treated group were administered twice, i.e., 30 minutes before and 45 minutes after administratin of 10 mg/kg of cisplatin (Sigma, U.S.A) dissolved in saline (3 ml/kg). The number of emetic episodes for 3 hours after administration of cisplatin was recorded, and the inhibition rate of the test compound was calculated as follows.

$$\text{Inhibition rate (\%)} = \left(1 - \frac{\text{mean number of emetic episodes in treated group}}{\text{mean number of emetic episodes in control group}}\right) \times 100$$

All test compounds were administered intravenously.

An acute toxicity test was performed using male Std-ddY mice weighing 25-30 g. Test compounds dissolved or suspended in 0.5% tragacanth solution were administered intraperitoneally. The mortality was observed for 7 days after the administration.

The results are shown in Table 2.

TABLE 2

| Effect on cisplatin-induced vomiting in ferrets and acute toxicity in mice | | |
|---|---|---|
| Test compound | Inhibition of emetic episodes in ferrets Inhibition rate (%) | Acute toxicity in mice [dose: 100 mg/kg (i.p.)] |
| 1(a)* | 89 | 1/5** |
| 8 | 71 | 0/5 |
| 16 | 82 | 0/5 |
| 17 | 62 | 1/5 |
| 32 | 62 | 0/5 |
| 33 | 44 | 2/5 |
| 53 | 29 | 1/5 |

*)The compound of Example 1 (a)
**)the number of dead animals/the number of animals used As can be seen from the test results given above, the compounds of formula (I) and their physiologically acceptable acid addition salts and quaternary ammonium salts have potent serotonin 3 (5-$HT_3$) receptor antagonizing activity, and can be used for the treatment and prevention of various diseases induced by stimulation of serotonin 3 (5-$HT_3$) receptor, for example the treatment and prevention of anorexia, nausea, vomiting and abdominal discomfort in acute and chronic gastritis, gastric and duodenal ulcer, gastric neurosis, and gastroptosis: And of esophageal and biliary duct disorders, urinary tract disorders and diarrhaea and constipation in irritable bowel syndrome or carcinoid syndrome. They can also be used for the treatment and prevention of nausea and vomiting following administration of anticancer agents such as cisplatin and X-ray irradiation, and motion sickness such as carsickness, seasickness and airsickness; cluster headache, migraine and trigeminal neuralgia; and the treatment of psychotic disorders such as anxiety, agonia, schizophrenia and mania, dementia, sensory disturbance, stress-related psychiatric disorders, cardiac disorders (such as arrhythmia and angina pectoris), obesity, lung embolism, rhinitis, seroton-induced rhinophathia, somolence, and pain. They can also be used to treat and prevent intoxication by addictive drugs such as morphine, nicotine and amphetamine.

They may be administered orally, parenterally or intrarectally. The clinical dose of the compound of formula (I) or its physiologically acceptable salt or quaternary ammonium salt varies with the type of the compound, the administration route, the severity of the disease, the age of the patient, etc. Usually, it is 0.0001 to 20 mg/kg/day, preferably 0.001 to 5 mg/kg/day.

The compound of formula (I) or its salt is usually administered in the form of a pharmaceutical composition prepared by admixing with pharmaceutically acceptable carriers. The pharmaceutical carriers may be those substances which are ordinarily used in the pharmaceutical field and do not react with the compound of formula (I) or its salt. Specific examples include ciric acid, glutaic acid, glycine, lactose, inositol, glucose, mannitol, dextrin, sorbitol, cyclodextrin, starch, sucrose, methyl p-hydroxybenzoate, magnesium aluminosilicate tetrahydrate, synthetic aluminum silicate, microcrystalline cellulose, sodium carboxymethylcellulose, hydroxypropyl starch, calcium carboxymethylcellulose, ion-exchange resins, methyl cellulose, gelatin, acacia, pullulan, hydroxypropylcellulose, hydroxypropylcellulose of a low degree of substitution, hydroxy propylmethylcellulose, polyvinylpyrrolidone, polyvinyl alcohol, light sillicic anhydride, magnesium stearate, talc, tragacanth, bentonite, veegum, carboxyvinyl polymer, titanium dioxide, sodium chloride, sorbitan fatty acid esters, sodium laurylsulfate, glycerol, fatty acid glycerides, purified lanolin, glycerogelatin, polysorbate, macrogol, vegetable oils, waxes, propylene glycol, ethanol, benzyl alcohol, sodium hydroxide and hydrochloric acid. The dosage forms of the pharmaceutical composition include tablets, capsules, granules, fine granules, powder, syrups, suspensions, injections, and suppositories. They are prepared by conventional methods. Liquid preparations may be dissolved or suspended in water or other suitable media before use. Tablets, granules and fine granules may be coated by known methods. These preparations may contain one or more other therapeuticaly active compounds.

The following Reference Examples and Examples illustrate the present invention more specifically. The invention should not be construed to be limited to these examples. In these examples, the compounds were identified by elemental analysis, mass spectrum, IR spectrum, UV spectrum, NMR spectrum, etc.

For simplification, the following abbreviations are sometmes used in these examples.

A: ethanol
AC: acetone
E: diethyl ether
M: methanol
Me: methyl group
Et: ethyl group
Ph: phenyl group
J: coupling constant
s: singlet
d: doublet
dd: double doublet
t: triplet
q: quartet
quint: quintet
m: multiplet
br: broad
q.s.: quantum sufficit

REFERENCE EXAMPLE 1

Preparation of 6-fluoro-1H-indazole-3-carboxylic acid:

6-Fluoroisatin prepared according to the method of J. Org. Chem., 21, 169 (1956) is added to a solution of sodium hydroxide (7.4 g) in water (130 ml), and the mixture obtained is gently heated until it dissolves.

After the solution is cooled to 0° C., a solution of sodium nitrite (13.8 g) in water (45 ml) is added dropwise to the reaction mixture, and this mixture is poured, in small portions with vigorous stirring, into the sulfuric acid (33.9 g) in water (430 ml) at 0° C. The mixture is stirred for 30 minutes at 0° C. A solution of stannous chloride (85.3 g) in hydrochloric acid (170 ml) is added dropwise to the reaction mixture at 0° C., and the mixture is stirred at 25° C. for 2 hours. The precipitates are collected and washed successively with water, acetone, and methanol, and dried to give the title compound (15.6 g), m.p. >290° C. Mass spectrum: m/z 180.

Various compounds of Reference Example 2 to 5 are prepared in substantially the same manner as in Reference Example 1, using the corresponding starting materials in place of 6-fluoroisatine.

REFERENCE EXAMPLE 2

4-chloro-1H-indazole-3-carboxylic acid. Mass spectrum: m/z 196.

REFERENCE EXAMPLE 3

6-chloro-1H-indazole-3-carboxylic acid. Mass spectrum: m/z 196.

REFERENCE EXAMPLE 4

7-chloro-1H-indazole-3-carboxylic acid, m.p. 243°-245° C.

REFERENCE EXAMPLE 5

5,6-difluoro-1H-indazole-3-carboxylic acid, m.p. 288°-293° C.

EXAMPLE 1

Preparation of N-[1-(3-methylbenzyl)-4-methylhexahydro-1H-1,4-diazepin-6-yl]-1H-indazole-3-carboxamide A solution of 6-acetylamino-1-(3-methylbenzyl)-4-methyl-hexahydro-1H-1,4-diazepine (0.9 g) in 10% hydrochloric acid (20 ml) is refluxed with stirring for 2 hours. After cooling, the reaction mixture is basified with 48% aqueous sodium hydroxide solution and extracted with chloroform. The organic layer is washed with water and dried over magnesium sulfate. The solvent is evaporated under reduced pressure to give an oil. A mixture of this oil, 1H-indazole-3-carboxylic acid (530 mg), 1-ethyl-3-(3-dimethylaminopropyl)carbodiimide hydrochloride (630 mg) and dichloromethane (20 ml) is stirred at 25° C. for 2 hours. The reaction mixture is washed successively with water and 10% aqueous sodium hydroxide solution, dried over magnesium sulfate, and evaporated under reduced pressure. The residue is chromatographed on silica gel with elution of acetone. Fractions containing the title compound are pooled and evaporated under reduced pressure to give the title compound (0.4 g) as an oil.

(a) The free base thus obtained is converted to the hemifumarate of the title compound in a usual manner, m.p. 190°-192° C. (recrystallized from ethanol).

$^1$H-NMR spectrum (DMSO-$D_6$, δppm): 2.20 (3H, s, —$CH_2C_6H_4C\underline{H_3}$), 2.41 (3H, s, —$NC\underline{H_3}$), 2.5-3.1 (8H, m), 3.63 (2H, s, —$NC\underline{H_2}C_6H_4CH_3$), 3.9-4.4 (1H, m, —CONHC$\underline{H}$—), 6.8-7.7 (7H, m), 8.16 (each 1H, each d, each J=8Hz, —CON$\underline{H}$—, 4-$\underline{H}$), 13-14 (1H, br s, —N$\underline{H}$).

(b) The free base obtained above is converted to the dihydrochloride of the title compound in a usual manner, m.p. 241°-244° C. (recrystallized from methanol-water).

EXAMPLE 2-26

Various compounds listed in the following Table 3 are prepared in substantially the same manner as in Example 1, using 1H-indazole-3-carboxylic acid and the corresponding 6-acetylamino-1-methylhexahydro-1H-1,4-diazepine derivatives.

TABLE 3

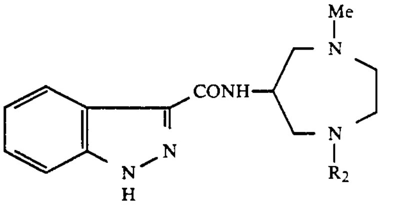

.Q

| Ex. | $R_2$ | Q | m.p. (°C.) | Recry. solv. |
|---|---|---|---|---|
| 2 | 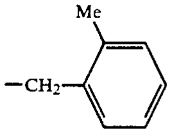 | oxalate. $H_2O$ | 103~106 | A-E |
| 3 | 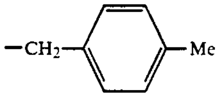 | hemi-fumarate | 234~237 | A |
| 4 | 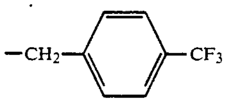 | hemi-fumarate. $\frac{1}{4}H_2O$ | 230~231 | A |
| 5 | 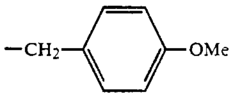 | hemi-fumarate | 196~198 | A |
| 6 | 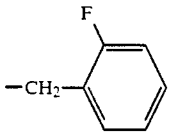 | oxalate. $\frac{3}{4}H_2O$ | 87~90 | A-E |
| 7 | 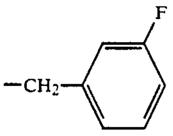 | hemi-fumarate | 169~171 | A |
| 8 | 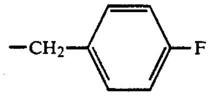 | hemi-fumarate | 205~207 | A |
| 9 | 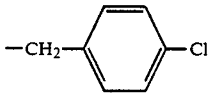 | hemi-fumarate. $1/5H_2O$ | 243~246 | M |
| 10 | 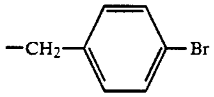 | hemi-fumarate | 241~244 | M |
| 11 | 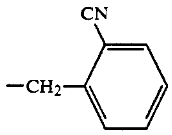 | oxalate. $\frac{1}{4}H_2O$ | 102~107 | A-E |

TABLE 3-continued

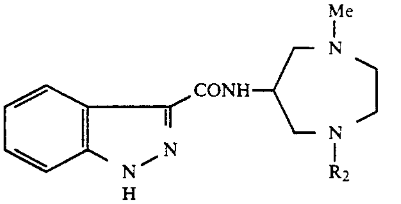

.Q

| Ex. | $R_2$ | Q | m.p. (°C.) | Recry. solv. |
|---|---|---|---|---|
| 12 | 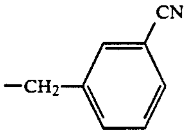 | fumarate. $\frac{1}{4}H_2O$ | 159~161 | A-AC |
| 13 | 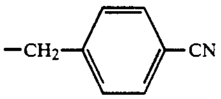 | hemi-fumarate. $\frac{1}{4}H_2O$ | 214~216 | M |
| 14 | 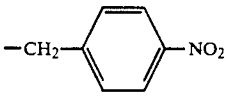 | hemi-fumarate. $\frac{1}{4}EtOH$ | 199~202 | A |
| 15 | 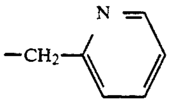 | sesqui-oxalate. $7/4H_2O$ | 95~100 | A-E |
| 16 | 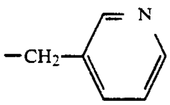 | 5/2 fumarate | 170~172 | A |
| 17 | 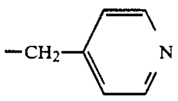 | di-fumarate. $\frac{1}{2}H_2O$ | 80~85 | A-E |
| 18 | 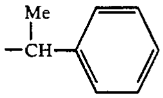 | oxalate. $5/4H_2O$ | 98~101 | A-E |
| 19 | 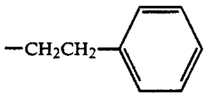 | sesqui-oxalate. $\frac{1}{2}H_2O$ | 99~102 | A-E |
| 20 | $-CH_2CH{=}CH_2$ | sesqui-oxalate. $\frac{1}{2}H_2O$ | 85~88 | A-E |
| 21 | 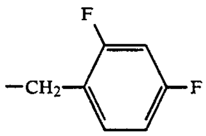 | dioxalate. $\frac{3}{4}H_2O$ | 118~121 | A |
| 22 | 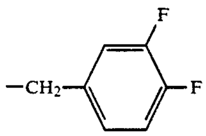 | hemi-fumarate. | 177~178 | A |

TABLE 3-continued

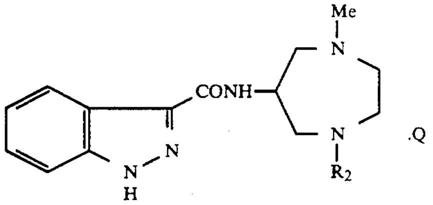

| Ex. | $R_2$ | Q | m.p. (°C.) | Recry. solv. |
|---|---|---|---|---|
| 23 | 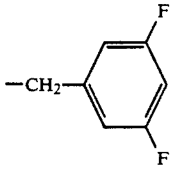 | fumarate. ¾$H_2O$ | 129~131 | A |
| 24 | 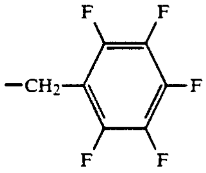 | — | 184~185 | AC |
| 25 | 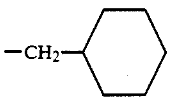 | dioxalate. ¼$H_2O$ | 109~111 | A-E |
| 26 | 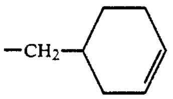 | sesqui-oxalate. ½$H_2O$ | 103~105 | A-E |

EXAMPLE 27

Preparation of N-[1-(2,5-dimethylbenzyl)-4-methylhexahydro-1H-1,4-diazepin-6-yl]-1H-indazole-3-carboxamide To a solution of 1H-indazole-3-carboxylic acid (1.0 g) in N,N-dimethylformamide (20 ml), N,N'-carbonyldiimidazole (1.1 g) is added, and the mixture is heated at 60° C. for 2 hours. 6-Amino-1-(2,5-dimethylbenzyl)-4-methylhexahydro-1H-1,4-diazepine (1.5 g) is added to the reaction mixture, and the mixture is heated at 60° C. for 2 hours. The solvent is evaporated under reduced pressure, and the residue is diluted with water and extracted with chloroform. The organic layer is washed successively with water and aqueous sodium hydroxide solution, and dried over sodium sulfate. The solvent is evaporated under reduced pressure, and the residue is chromatographed on silica gel with elution of acetone. Fractions containing the title compound are pooled and evaporated under reduced pressure to give the title compound (1.6 g) as an oil. The free base thus obtained is converted to the fumarate of the title compound in a usual manner, m.p. 168°-170° C. (recrystallized from ethanol).

$^1$H-NMR spectrum (DMSO-$D_6$, δppm): 2.15, 2.30 [each 3H, each s, —$CH_2C_6H_3(\underline{CH_3})_2$], 2.40 (3H, s, —$N\underline{CH_3}$), 3.50 [2H, s, —$N\underline{CH_2}C_6H_3(CH_3)_2$], 4.2 (1H, m, —CONHC$\underline{H}$—), 6.7-7.7 (5H, m), 8.03 (1H, d, J=8Hz, —CON$\underline{H}$—), 8.14 (1H, d, J=8Hz, 4-$\underline{H}$), 11.5 (1H, br s, —N$\underline{H}$).

EXAMPLE 28

Preparation of N-(1,4-dimethylhexahydro-1H-1,4-diazepin-6-yl)-1H-indazole-3-carboxamide Difumarate ¼ hydrate of the title compound is prepared in substantially the same manner as in Example 27, using 6-amino-1,4-dimethylhexahydro-1H-1,4-diazepine in place of 6-amino-1-(2,5-dimethylbenzyl)-4-methylhexahydro-1H-1,4-diazepine in Example 27, m.p. 153°-155° C. (recrystallized from ethanol).

$^1$H-NMR spectrum (DMSO-$D_6$, δppm): 2.43 [6H, s, 2(—N$\underline{CH_3}$)], 2.6-3.1 (8H, m), 4.34 (1H, m, —CONH-C$\underline{H}$—), 7.1-7.8 (3H, m, 5-$\underline{H}$, 6-$\underline{H}$, 7-$\underline{H}$), 8.0-8.4 (2H, m, —CON$\underline{H}$—, 4-$\underline{H}$).

EXAMPLE 29

Preparation of N-(1,4-dibenzylhexahydro-1H-1,4-diazepin-6-yl)-1H-indazole-3-carboxamide The title compound is prepared in substantially the same manner as in Example 1, using 6-acetylamino-1,4-dibenzylhexahydro-1H-1,4-diazepine in place of 6-acetylamino-1-(3-methylbenzyl)-4-methylhexahydro-1H-1,4-diazepine in Example 1, m.p. 115°-116° C. (recrystallized from ethanol).

$^1$H-NMR spectrum (DMSO-$D_6$, δppm): 2.4-2.9 (4H, m), 3.00[4H, t, J=4Hz, 2(—N$\underline{CH_2}$—)], 3.67 [4H, s, 2(—N$\underline{CH_2}$Ph)], 4.2-4.7 (1H, m, —CONHC$\underline{H}$—), 7.0-7.5 [13H, m, 5-$\underline{H}$, 6-$\underline{H}$, 7-$\underline{H}$, 2(—$CH_2C_6\underline{H_5}$)], 8.36 (1H, d, J=9Hz, 4-$\underline{H}$), 8.50 (1H, d, J=9Hz, —CON$\underline{H}$—), 11-13 (1H, br s, —N$\underline{H}$).

EXAMPLE 30

Preparation of N-(1-methylhexahydro-1H-1,4-diazepin-6-yl)-1H-indazole-3-carboxamide N-(1-Benzyl-4-methylhexahydro-1H-1,4-diazepin-6-yl)-1H-indazole-3-carboxamide (850 mg) is dissolved in ethanol (40 ml) and hydrogenated over 10% palladium on carbon (100 mg) at about 50° C. After the calculated amount of the hydrogen is absorbed, the catalyst is filtered off. The filtrate is evaporated under reduced pressure to give the title compound as an oil. The free base thus obtained is converted to the oxalate 3/2 hydrate of the title compound in a usual manner, m.p. 163°-166° C. (recrystallized from ethanol-diethyl ether).

EXAMPLE 31

Preparation of N-(hexahydro-1H-1,4-diazepin-6-yl)-1H-indazole-3-carboxamide

The 5/4 oxalate ½ hydrate of title compound is prepared in substantially the same manner as in Example 30, using N-(1,4-dibenzylhexahydro-1H-1,4-diazepin-6-yl)-1H-indazole-3-carboxamide in place of N-(1-benzyl-4-methylhexahydro-1H-1,4-diazepin-6-yl)-1H-indazole-3-carboxamide in Example 30, m.p. 219°-222° C. (recrystallized from ethanol-diethyl ether).

EXAMPLE 32

Preparation of N-(1-benzyl-4-methylhexahydro-1H-1,4-diazepin-6-yl)-1H-indazole-3-carboxamide:

To a solution of 6-amino-1-benzyl-4-methylhexahydro-1H-1,4-diazepine (1.0 g) in dichloromethane (20 ml), 1H-indazole-3-carboxylic acid (740 mg) and 1-ethyl-3-(3-dimethylaminopropyl)carbodiimide hydrochloride (877 mg) are added, and the resulting mixture is stirred at 25° C. for 2 hours. The reaction mixture is washed successively with water and 10% aqueous sodium hydroxide solution, and dried over magnesium sulfate. The solvent is evaporated under reduced pressure, and the residue is chromatographed on silica gel with elution of acetone. Fractions containing the title compound are pooled and evaporated under reduced pressure to give the title compound (0.9 g) as an oil. The free base thus obtained is converted to the hemifumarate of the title compound in a usual manner, m.p. 192°-194° C. (recrystallized from ethanol).

$^1$H-NMR spectrum (DMSO-$D_6$, δppm): 2.40 (3H, s, —NC$\underline{H}_3$), 2.3-3.0 (8H, m), 3.70 (2H, s, —NC$\underline{H}_2$Ph), 4.0-4.4 (1H, m, —CONHC$\underline{H}$—), 7.1-7.5 (8H, m, 5-$\underline{H}$, 6-$\underline{H}$, 7-$\underline{H}$, —$CH_2C_6\underline{H}_5$), 8.16 (each 1H, each d, each J=9Hz, 4-$\underline{H}$, —CON$\underline{H}$—), 13.5 (1H, br s, —N$\underline{H}$).

EXAMPLE 33

Preparation of N-(1-benzyl-4-methylhexahydro-1H-1,4-diazepin-6-yl)-1-methyl-1H-indazole-3-carboxamide Oxalate ¼ ethanol 3/2 hydrate of the title compound is prepared in substantially the manner as in Example 32, using 1-methyl-1H-indazole-3-carboxylic acid in place of 1H-indazole-3-carboxylic acid in Example 32, m.p. 80°-85° C. (recrystallized from ethanol-diethyl ether).

$^1$H-NMR spectrum (DMSO-$D_6$, δppm): 2.30 (3H, s, —NC$\underline{H}_3$), 2.1-3.5 (8H, m), 3.75 (2H, s, —NC$\underline{H}_2$Ph), 4.16 (3H, s, —NC$\underline{H}_3$), 4.2-4.7 (1H, m, —CONHC$\underline{H}$—), 7.1-7.6 (7H, m), 7.76 (1H, d, J=8Hz, 7-$\underline{H}$), 8.16 (1H, d, J=8Hz, 4-$\underline{H}$), 8.92 (1H, d, J=9Hz, —CON$\underline{H}$—).

EXAMPLE 34

Preparation of N-(1,4-dimethylhexahydro-1H-1,4-diazepin-6-yl)-1-methyl-1H-indazole-3-carboxamide 3/2 Fumarate of the title compound is prepared in substantially the same manner as in Example 1, using 1-methyl-1H-indazole-3-carboxylic acid and 6-acetylamino-1,4-dimethylhexahydro-1H-1,4-diazepine in place of 1H-indazole-3-carboxylic acid and 6-acetylamino-1-(3-methylbenzyl)-4-methylhexahydro-1H-1,4-diazepine in Example 1, m.p. 176°-180° C. (recrystallized from ethanol).

EXAMPLE 35

Preparation of N-(1-benzyl-4-methylhexahydro-1H-1,4-diazepin-6-yl)-1-ethyl-1H-indazole-3-carboxamide A mixture of 1-ethyl-1H-indazole-3-carboxylic acid (8.6 g), thionyl chloride (8 ml) and chloroform (80 ml) is refluxed for 1 hour. After removal of solvent, the residue is dissolved in dichloromethane (100 ml), and a solution of 6-amino-1-benzyl-4-methylhexahydro-1H1,4-diazepine (9.9 g) and triethylamine (9.2 g) in dichloromethane (100 ml) is added dropwise to the mixture at 0° C. The reaction mixture is stirred at 25° C. for 2 hours, washed with water, and dried over sodium sulfate. The solvent is evaporated under reduced pressure, and the residue is chromatographed on silica gel with elution of acetone. Fractions containing the title compound are pooled and evaporated under reduced pressure to give the title compound (13.6 g) as an oil.

(a) The free base thus obtained is converted to the fumarate of the title compound in a usual manner, m.p. 135°-137° C. (recrystallized from ethanol).

$^1$H-NMR spectrum (DMSO-$D_6$, δppm): 1.48 (3H, t, J=7Hz, —$CH_2C\underline{H}_3$), 2.44 (3H, s, —NC$\underline{H}_3$), 2.6-3.2 (8H, m), 3.66 (2H, s, —NC$\underline{H}_2$Ph), 4.0-4.5 (1H, m, —CONHC$\underline{H}$—), 4.54 (2H, q, J=7Hz, —C$\underline{H}_2CH_3$), 7.1-7.6 (7H, m), 7.76 (1H, d, J=8Hz, 7-$\underline{H}$), 8.14 (each 1H, each d, each J=9Hz, 4-$\underline{H}$, —CON$\underline{H}$—).

(b) The free base obtained above is converted to the 3/2 oxalate ¾ hydrate of the title compound in a usual manner, m.p. 77°-81° C. (recrystallized from ethanol-diethyl ether).

EXAMPLE 36

Preparation of N-(1-methylhexahydro-1H-1,4-diazepin-6-yl)-1-ethyl-1H-indazole-3-carboxamide 3/2 Oxalate ¾ hydrate of the title compound is prepared in substantially the same manner as in Example 30, using N-(1-benzyl-4-methylhexahydro-1H-1,4-diazepin-6-yl)-1-ethyl-1H-indazole-3-carboxamide in place of N-(1-benzyl-4-methylhexahydro-1H-1,4-diazepin-6-yl)-1H-indazole-3-carboxamide in Example 30, m.p. 107°-111° C. (recrystallized from ethanol-diethyl ether).

$^1$H-NMR spectrum (DMSO-$D_6$, δppm): 1.46 (3H, t, J=7Hz, —$CH_2C\underline{H}_3$), 2.48 (3H, s, —NC$\underline{H}_3$), 2.7-3.5 (8H, m), 4.54 (3H, q, J=7Hz, —C$\underline{H}_2CH_3$, —CONHC$\underline{H}$—), 7.1-7.6 (2H, m, 5-$\underline{H}$, 6-$\underline{H}$), 7.78 (1H, d, J=8Hz, 7-$\underline{H}$), 8.16 (1H, d, J=8Hz, 4-$\underline{H}$), 8.38 (1H, d, J=9Hz, —CON$\underline{H}$—).

EXAMPLE 37

Preparation of N-[1-(3-methylbenzyl)-4-methylhexahydro-1H-1,4-diazepin-6-yl]-1-ethyl-1H-indazole-3-carboxamide A mixture of N-(1-methylhexahydro-1H-1,4-diazepin-6-yl)-1-ethyl-1H-indazole-3-carboxamide (1.8 g), potassium carbonate (4.1 g), sodium iodide (0.9 g), 3-methylbenzyl chloride (0.85 g) and methyl ethyl ketone (100 ml) is refluxed with stirring for 6 hours. After cooling, the reaction mixture is filtered, and the filtrate is concentrated under reduced pressure. The residue is chromatographed on silica gel with elution of chloroform-methanol (20:1). Fractions containing the title compound are pooled and evaporated under reduced pressure to give the title compound (1.9 g) as an oil. The free base thus obtained is converted to the fumarate of the title compound in a usual manner, m.p. 135°-137° C. (recrystallized from ethanol-diethyl ether).

$^1$H-NMR spectrum (DMSO-$D_6$, δppm): 1.48 (3H, t, J=7Hz, —$CH_2C\underline{H}_3$), 2.20 (3H, s, —$CH_2C_6H_4C\underline{H}_3$), 2.43 (3H, s, —NC$\underline{H}_3$), 2.6-3.1 (8H, m), 3.64 (2H, s, —C$\underline{H}_2C_6H_4CH_3$), 4.0-4.5 (1H, m, —CONHC$\underline{H}$—), 4.55 (2H, q, J=7Hz, —C$\underline{H}_2CH_3$), 6.8-7.6 (7H, m), 7.75 (1H, d, J=8Hz, 7-$\underline{H}$), 8.13 (each 1H, each d, each J=9Hz, 4-$\underline{H}$, —CON$\underline{H}$—).

EXAMPLE 38-42

Various compounds listed in the following Table 4 are prepared in substantially the same manner as in Example 37, using N-(1-methylhexahydro-1H-1,4-diazepin-6-yl)-1-ethyl-1H-indazole-3-carboxamide and the appropriate arylalkylating, heteroarylalkylating or alkylating agents.

TABLE 4

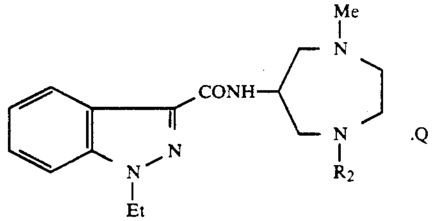

| Ex. | $R_2$ | Q | m.p. (°C.) | Recry. solv. |
|---|---|---|---|---|
| 38 | 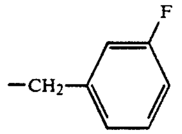 | fumarate | 127~129 | A |
| 39 | 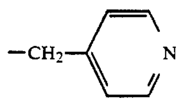 | difumarate. $\frac{1}{4}H_2O$ | 122~127 | A |
| 40 | 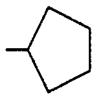 | dioxalate | 94~97 | A-E |
| 41 | 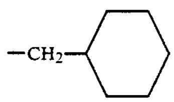 | sesqui-oxalate. $\frac{1}{2}H_2O$ | 103~106 | A-E |
| 42 | 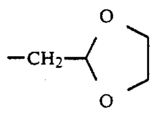 | sesqui-oxalate | 73~79 | A-E |

EXAMPLE 43

Preparation of N-(1-benzoyl-4-methylhexahydro-1H-1,4-diazepin-6-yl)-1-ethyl-1H-indazole-3-carboxamide To a solution of N-(4-methylhexahydro-1H-1,4-diazepin-6-yl)-1-ethyl-1H-indazole-3-carboxamide (1.0 g) in dichloromethane (20 ml), benzoic anhydride (1.5 g) is added, and the mixture is stirred at 25° C. for 16 hours. The reaction mixture is washed with saturated sodium bicarbonate, and dried over sodium sulfate. The solvent is evaporated under reduced pressure, and the residue is chromatographed on silica gel with elution of acetone. Fractions containing the title compound are pooled and evaporated under reduced pressure to give the title compound (1.3 g) as an oil. The free base thus obtained is converted to the oxalate ¾ hydrate of the title compound in a usual manner, m.p. 100°–103° C. (recrystallized from ethanol-diethyl ether).

$^1$H-NMR spectrum (DMSO-$D_6$, δppm): 1.45 (3H, t, J=8Hz, —$CH_2C\underline{H_3}$), 2.72 (3H, s, —$NC\underline{H_3}$), 2.6–4.2 (8H, m), 4.52 (2H, q, J=8Hz, —$C\underline{H_2}CH_3$), 7.52 (5H, s, —$COC_6\underline{H_5}$) 7.1-7.6 (2H, m, 5-H, 6-H), 7.76 (1H, d, J=8Hz, 7-H), 8.12 (1H, d, J=8Hz, 4-H), 8.47 (1H, d, J=8Hz, —CONH—).

EXAMPLE 44-51

Various compounds listed in the following Table 5 are prepared in substantially the same manner as in Example 32, using 6-amino-1-benzyl-4-methylhexahydro-1H-1,4-diazepine and the corresponding 1H-indazole-3-carboxylic acid derivatives.

TABLE 5

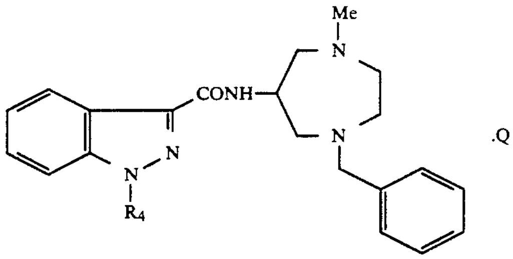

| Ex. | $R_4$ | Q | m.p. (°C.) | Recry. solv. |
|---|---|---|---|---|
| 44 | —$CH_2CH_2CH_3$ | sesqui-oxalate. $\frac{1}{2}H_2O$ | 70~76 | A-E |
| 45 | 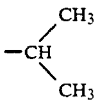 | sesqui-oxalate. $\frac{3}{4}H_2O$ | 77~80 | A-E |
| 46 | —$CH_2CH_2CH_2CH_3$ | sesqui-oxalate. $\frac{1}{2}H_2O$ | 69~74 | A-E |
| 47 | 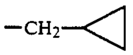 | 5/4oxalate. 5/4$H_2O$ | 72~75 | A-E |
| 48 | —$CH_2CH{=}CH_2$ | sesqui-oxalate. $\frac{1}{2}H_2O$ | 73~77 | A-E |
| 49 | 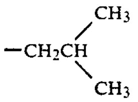 | sesqui-oxalate. $\frac{1}{2}H_2O$ | 82~85 | A-E |
| 50 | 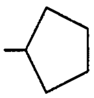 | sesqui-oxalate. $\frac{1}{4}H_2O$ | 86~90 | A-E |
| 51 | 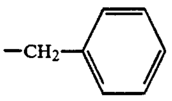 | sesqui-oxalate. $\frac{1}{4}H_2O$ | 76~79 | A-E |

EXAMPLE 52

Preparation of N-(1-benzyl-4-methylhexahydro-1H-1,4-diazepin-6-yl)-1-acetyl-1H-indazole-3-carboxamide To a solution of N-(1-benzyl-4-methylhexahydro-1H-1,4-diazepin-6-yl)-1H-indazole-3-carboxamide (1.0 g) in dichloromethane (10 ml), acetic anhydride (0.56 g) is added; and the mixture is stirred at 25° C. for 16 hours. The reaction mixture is washed with saturated sodium bicarbonate and dried over sodium sulfate. The solvent is evaporated under reduced pressure, and the residue is chromatographed on silica gel with elution of acetone. Fractions containing the title compound are pooled and evaporated under reduced pressure to give the title compound (0.92 g) as an oil. The free base thus obtained is converted to the fumarate ¼ hydrate of the title compound in a usual manner, m.p. 166°-168° C. (recrystallized from ethanol).

EXAMPLE 53

Preparation of
N-(1-benzyl-4-methylhexahydro-1H-1,4-diazepin-6-yl)-1-propionyl-1H-indazole-3-carboxamide Fumarate of the title compound is prepared in substantially the same manner as in Example 52, using propionic anhydride in place of acetic anhydride in Example 52, m.p. 185°-187° C. (recrystallized from ethanol).

$^1$H-NMR spectrum (DMSO-$D_6$, δppm): 1.25 (3H, t, J=7Hz, —$COCH_2CH_3$), 2.45 (3H, s, —$NCH_3$), 2.6-3.1 (8H, m), 3.31 (2H, q, J=7Hz, —$COCH_2CH_3$), 3.69 (2H, s, —$CH_2Ph$), 4.1-4.5 (1H, m, —CONHCH—), 7.1-7.8 (7H, m, 5-H, 6-H, —$CH_2C_6H_5$), 8.1-8.6 (3H, m, 4-H, 7-H, —CONH—).

EXAMPLE 54

Preparation of
N-(1-benzyl-4-methylhexahydro-1H-1,4-diazepin-6-yl)-1-benzoyl-1H-indazole-3-carboxamide Fumarate ½ hydrate of the title compound is prepared in substantially the same manner as in Example 52, using benzoic anhydride in place of acetic anhydride in Example 52, m.p. 187°-189° C. (recrystallized from ethanol).

$^1$H-NMR spectrum (DMSO-$D_6$, δppm): 2.40 (3H, s, —$NCH_3$), 2.6-3.2 (8H, m), 3.60 (2H, s, —$CH_2Ph$), 3.9-4.4 (1H, m, —CONHCH—), 7.12 (4H, m), 7.4-7.9 (4H, m), 7.9-8.6 (5H, m).

EXAMPLE 55

Preparation of
N-(1-benzyl-4-methylhexahydro-1H-1,4-diazepin-6-yl)-1-methoxycarbonyl-1H-indazole-3-carboxamide To a solution of N-(1-benzyl-4-methylhexahydro-1H-1,4-diazepin-6-yl)-1H-indazole-3-carboxamide (0.92 g) and triethylamine (0.77 g) in dichloromethane (30 ml), methyl chloroformate (0.48 g) is added dropwise at 0° C., and the mixture is stirred at 25° C. for 16 hours. The reaction mixture is washed with saturated sodium bicarbonate and dried over sodium sulfate. The solvent is evaporated under reduced pressure, and the residue is chromatographed on silica gel with elution of acetone. Fractions containing the title compound are pooled and evaporated under reduced pressure to give the title compound (0.7 g) as an oil. The free base thus obtained is converted to the fumarate of the title compound in a usual manner, m.p. 158°-160° C. (recrystallized from ethanol).

$^1$H-NMR spectrum (DMSO-$D_6$, δppm): 2.40 (3H, s, —$NCH_3$), 2.6-3.1 (8H, m), 3.66 (2H, s, —$CH_2Ph$), 4.13 (3H, s, —$COOCH_3$), 4.0-4.4 (1H, m, —CONHCH—), 7.1-7.9 (7H, m), 8.1-8,5 (3H, m).

EXAMPLE 56

Preparation of
N-(1-benzyl-4-methylhexahydro-1H-1,4-diazepin-6-yl)-1-(2-butanon-3-yl)-1H-indazole-3-carboxamide To a solution of N-(1-benzyl-4-methylhexahydro-1H-1,4-diazepin-6-yl)-1-1H-indazole-3-carboxamide (1.0 g) in tetrahydrofuran (20 ml), potassium tert-butoxide (0.32 g) is added at 0° C., and the mixture is stirred at the same temperature for 30 minutes. 3-Chloro-2-butanone (0.29 g) is added to the mixture at 0° C. and stirred at 25° C. for 16 hours. The reaction mixture is washed with water and dried over sodium sulfate. The solvent is evaporated under reduced pressure, and the residue is chromatographed on silica gel with elution of acetone. Fractions containing the title compound are pooled and evaporated under reduced pressure to give the title compound (0.54 g) as an oil. The free base thus obtained is converted to the 3/2 oxalate ¼ hydrate of the title compound in a usual manner, m.p. 97°-100° C. (recrystallized from ethanol-diethyl ether).

$^1$H-NMR spectrum (DMSO-$D_6$, δppm): 1.76 (3H, d, J=7Hz, —$CHCH_3$), 2.02 (3H, s, —$COCH_3$), 2.80 (3H, s, —$NCH_3$), 2.6-3.5 (8H, m), 3.75 (2H, s, —$CH_2Ph$), 4.46 (1H, m, —CONHCH—), 5.77 (1H, q, J=7Hz, —$CHCH_3$), 7.1-7.6 (7H, m, 5-H, 6-H, —$CH_2C_6H_5$), 7.74 (1H, d, J=8Hz, 7-H), 8.16 (1H, J=8Hz, 4-H), 8.40 (1H, d, J=8Hz, —CONH—).

EXAMPLE 57

Preparation of
N-(1-benzyl-4-methylhexahydro-1H-1,4-diazepin-6-yl)-1-(2-hydroxyethyl)-1H-indazole-3carboxamide Oxalate ½ hydrate of the title compound is prepared in substantially the same manner as in Example 56, using 2-chloroethanol in place of 3-chloro-2-butanone in Example 56, m.p. 84°-89° C. (recrystallized from ethanol-diethyl ether).

$^1$H-NMR spectrum (DMSO-$D_6$, δppm): 2.81 (3H, s, —$NCH_3$), 2.6-3.5 (8H, m), 3.76 (2H, s, —$CH_2Ph$), 3.90 (2H, t, J=6Hz, —$CH_2CH_2OH$), 4.54 (2H, t, J=6Hz, —$CH_2CH_2OH$), 6.9-7.9 (7H, m), 7.75 (1H, d, J=8Hz, 7-H), 8.14 (1H, d, J=8Hz, 4-H), 8.41 (1H, d, J=8Hz, —CONH—).

EXAMPLE 58-65

Various compounds listed in the following Table 6 are prepared in substantially the same manner as in Example 32, using 6-amino-1-benzyl-4-methylhexahydro-1H-1,4-diazepine and the corresponding substituted 1H-indazole-3-carboxylic acids.

TABLE 6

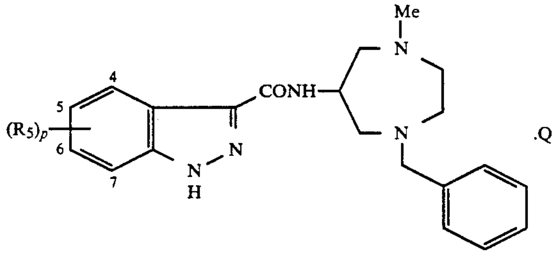

| Ex. | $(R_5)_p$ | Q | m.p. (°C.) | Recry. solv. |
|---|---|---|---|---|
| 58 | 5-F | dioxalate.¼EtOH.¼$H_2O$ | 118~121 | A-AC |
| 59 | 4-Cl | dioxalate.EtOH | 108~111 | A-AC |
| 60 | 5-Cl | sesquioxalate.¼EtOH.½$H_2O$ | 142~146 | A-AC |
| 61 | 6-Cl | dioxalate.¼$H_2O$ | 119~124 | A-AC |
| 62 | 7-Cl | dioxalate.½$H_2O$ | 145~148 | A-AC |
| 63 | 5-Me | dioxalate.¾$H_2O$ | 112~115 | A-AC |
| 64 | 6-F | dioxalate | 126~130 | A-AC |
| 65 | 5-F | dioxalate.½EtOH.¾$H_2O$ | 120~123 | A-AC |

EXAMPLE 66

Preparation of
N-(1-benzyl-3,4-dimethylhexahydro-1H-1,4-diazepin-6-yl)-1H-indazole-3-carboxamide To a solution of 1H-indazole-3-carboxylic acid (2.2 g) in N,N-dimethylformamide (40 ml), N,N'-carbonyldiimidazole (2.2 g) is added, and the mixture is heated at 60° C. for 3.5 hours. A solution of 6-amino-1-benzyl-3,4-dimethylhexahydro-1H-1,4-diazepine (3.0 g) in N,N-dimethylformamide (10 ml) is added to the mixture, and the mixture is stirred at 25° C. for 2 hours. The solvent is evaporated under reduced pressure, and the residue is diluted with water and extracted with chloroform. The organic layer is washed successively with 10% aqueous sodium hydroxide solution, water and saturated aqueous sodium chloride solution, and dried over sodium sulfate. The solvent is evaporated under reduced pressure, and the residue is chromatographed on silica gel with elution 10% methanol-acetone. Fractions containing the title compound are pooled and evaporated under reduced pressure to give the title compound (0.9 g) which is one isomer with lower polarity in two isomers produced in the above reaction, m.p. 203°-205° C. (recrystallized from isopropyl alcohol).

EXAMPLE 67

Preparation of
N-(1-benzyl-3,4-dimethylhexahydro-1H-1,4-diazepin-6-yl)-1H-indazole-3-carboxamide The title compound (1.9 g) is obtained by the same silica gel column chromatography in Example 66 as the other isomer with higher polarity in two isomers produced in the reaction of Example 66, m.p. 162°-163° C. (recrystallized from ethanol).

EXAMPLE 68

Preparation of
N-(1-benzyl-2,4-dimethylhexahydro-1H-1,4-diazepin-6-yl)-1H-indazole-3-carboxamide ¼ Hydrate of the title compound which is one isomer with lower polarity is prepared in substantially the same manner as in Example 66, using 6-amino-1-benzyl-2,4-dimethylhexahydro-1H-1,4-diazepine in place of 6-amino-1-benzyl-3,4-dimethylhexahydro-1H-1,4-diazepine in Example 66, m.p. 199°-202° C. (recrystallized from isopropyl alcohol).

EXAMPLE 69

Preparation of
N-(1-benzyl-2,4-dimethylhexahydro-1H-1,4-diazepin-6-yl)-1H-indazole-3-carboxamide The title compound is obtained by the same silica gel column chromatography in Example 68 as the other isomer with higher polarity, m.p. 164°-165° C. (recrystallized from toluene).

EXAMPLE 70

Preparation of
(1,4-dimethylhexahydro-1H-1,4-diazepin-6-yl) 1H-indazole-3-carboxylate To a solution of 1,4-dimethy-6-hydroxyhexahydro-1H-1,4-diazepine (1.9 g) in anhydrous tetrahydrofuran (10 ml), a solution of n-butyllithium in hexane (9.4 g) is added dropwise under nitrogen stream at 25° C., and the mixture is stirred for 30 minutes at the same temperature. To the reaction mixture is added dropwise, the reaction mixture prepared by the following method; to a solution of 1H-indazole-3-carboxylic acid (2.0 g) in anhydrous N,N-dimethylformamide (20 ml), N,N'-carbonyldiimidazole (2.0 g) is added at 25° C., and the mixture is heated at 80° C. for 4.5 hours and cooled to 25° C. The resulting reaction mixture is refluxed with stirring for 1 hour. Tetrahydrofuran is evaporated under reduced pressure, and the residue is diluted with water, extracted with diethyl ether. The organic layer is washed with saturated sodium chloride solution and dried over magnesium sulfate. The solvent is evaporated under reduced pressure, and the residue is chromatographed on silica gel with elution of chloroform-methanol (9:1). Fractions containing the title compound are pooled and evaporated under reduced pressure to give the title compound (2.4 g) as an oil. The free base is converted to 5/2 fumarate ¼ ethanol of the title compound in a usual manner, m.p. 184°-185° C. (recrystallized from ethanol).

EXAMPLE 71

A solution of Diindazole[2,3-a,2',3'-d]pirazine-7,14-dione (25 g) and 6-amino-4-(3-methylbenzyl)-1-methylhexahydro-1,4-diazepine (40.5 g) in N,N -dimethylformamide (250 ml) is heated at 60°-80° C. for 5 hours. The solvent is evaporated under reduced pressure, and the residue is dissolved in chloroform. The solution is washed with water and saturated sodium chloride solution, and dried over magnesium sulfate. The solvent is evaporated under reduced pressure. The oil thus obtained is purified by silica gel chromatography in the same manner as in Example 1 to give the title compound in Example 1.

EXAMPLE 72

Preparation of
6-acetylamino-1-benzyl-4-methylhexahydro-1H-1,4-diazepine

To a solution of 2-chloromethyl-1-benzyl-4-methylpiperazine (6.1 g) prepared according to the method of Helv. Chim. Acta, 45, 2383-2402 (1962) in acetonitrile (60 ml), sodium azide (3.3 g) is added, and the mixture is refluxed for 2 hours. The reaction mixture is filtered, and the filtrate is concentrated under reduced pressure. The residue is dissolved in toluene (100 ml), and a solution of 70% sodium bis(2-methoxyethoxy) aluminum hydride in toluene (10.4 g) is added in small portions to the above solution at 0° C. The resulting mixture is stirred at 25° C. for 3 hours, and then poured into ice-water, and 48% aqueous sodium hydroxide solution is added to the resulting solution. The aqueous layer is extracted with toluene, and the combined organic layer is dried over sodium sulfate. The solvent is evaporated under reduced pressure. The residue is dissolved in chloroform (200 ml), and acetic anhydride (5.2 g) is added to the solution. The mixture is stirred at 25° C. for 2 hours, washed successively with 48% aqueous sodium hydroxide solution and water, and dried over magnesium sulfate. The solvent is evaporated under reduced pressure, and the residue is chromatographed on silica gel with elution of chloroform-methanol (20:1). Fractions containing the title compound are pooled and evaporated under reduced pressure to give the title compound (1.0 g) as an oil.

$^1$H-NMR spectrum ($CDCl_3$, δppm): 1.85 (3H, s, $—COC\underline{H}_3$), 2.35 (3H, s, $—NC\underline{H}_3$), 3.46, 3.72 (each 1H, each d, each J=13Hz, $-CH_2Ph$), 3.98 (1H, m, $-CONHCH-$), 6.35 (1H, d, $-CONH-$), 7.30 (5H, m, $-CH_2C_6H_5$).

EXAMPLE 73

Preparation of 6-acetylamino-1,4-dimethylhexahydro-1H-1,4-diazepine

The title compound as an oil is prepared in substantially the same manner as in Example 72, using 2-chloromethyl-1,4-dimethylpiperazine in place of 2-chloromethyl-1-benzyl-4-methylpiperazine in Example 72.

$^1$H-NMR spectrum ($CDCl_3$, δppm): 2.02 (3H, s, $-COCH_3$), 2.37 [(6H, s, 2($-NCH_3$)], 2.32-2.52 (2H, m), 2.56-2.66, 2.72-2.83 (6H, m), 4.04-4.12 (1H, m, $-CONHCH-$).

EXAMPLE 74

Preparation of 6-acetylamino-1-methylhexahydro-1H-1,4-diazepine

6-Acetylamino-1-benzyl-4-methylhexahydro-1H-1,4-diazepine (20 g) is dissolved in ethanol (400 ml) and acetic acid (70 ml), and hydrogenated over 10% palladium on carbon (2 g) at about 50° C. After the calculated amount of the hydrogen is absorbed, the catalyst is filtered off. The filtrate is evaporated under reduced pressure to give acetate of the title compound (30 g) as an oil.

EXAMPLE 75

Preparation of 6-acetylamino-1,4-diethylhexahydro-1H-1,4-diazepine

The title compound as an oil is prepared in substantially the same manner as in Example 72, using 2-chloromethyl-1,4-diethylpiperazine in place of 2-chloromethyl-1-benzyl-4-methylpiperazine in Example 72.

EXAMPLE 76

Preparation of 6-acetylamino-1,4-dibenzylhexahydro-1H-1,4-diazepine

The title compound as an oil is prepared in substantially the same manner as in Example 72, using 2-chloromethyl-1,4-dibenzylpiperazine in place of 2-chloromethyl-1-benzyl-4-methylpiperazine in Example 72.

EXAMPLE 77

Preparation of 6-acetylamino-1-(3-methylbenzyl)-4-methylhexahydro-1H-1,4-diazepine A mixture of acetate of 6-acetylamino-1-methylhexahydro-1H-1,4-diazepine (3.0 g), 3-methylbenzyl chloride (3.5 g), potassium carbonate (17 g), sodium iodide (0.1 g) and methyl ethyl ketone (200 ml) is refluxed with stirring for 16 hours. The reaction mixture is filtered, and the filtrate is concentrated under reduced pressure. The residue is chromatographed on silica gel with elution of chloroform-methanol (20:1). Fractions containing the title compound are pooled and evaporated under reduced pressure to give the title compound as an oil.

$^1$H-NMR spectrum ($CDCl_3$, δppm): 1.86 (3H, s, $-COCH_3$), 2.34 (3H, s, $-CH_2C_6H_4CH_3$), 2.36 (3H, s, $-NCH_3$), 3.43, 3.67 (each 1H, each d, J=12Hz, $-CH_2C_6H_4CH_3$), 3.97 (1H, m, $-CONHCH-$), 6.45 (1H, d, $-CONH-$), 7.0-7.4 (4H, m, $-CH_2C_6H_4CH_3$).

EXAMPLE 78-104

Various compounds listed in Table 7 are prepared in substantially the same manner as in Example 77, using the appropriate alkylating, arylalkylating, or heteroaryl-alkylating agents in place of 3-methylbenzyl chloride in Example 77.

TABLE 7

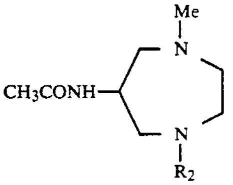

| Ex. | $R_2$ |
|---|---|
| 78 | 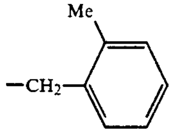 |
| 79 | 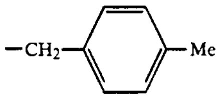 |
| 80 | 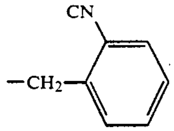 |
| 81 | 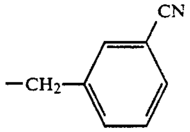 |
| 82 | 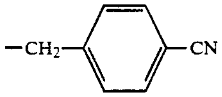 |
| 83 | 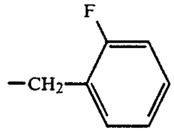 |
| 84 | 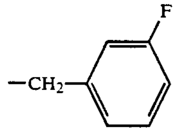 |
| 85 | 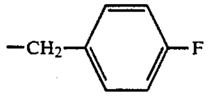 |
| 86 | 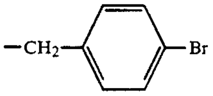 |

TABLE 7-continued

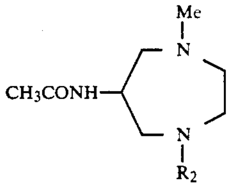

| Ex. | $R_2$ |
|---|---|
| 87 | 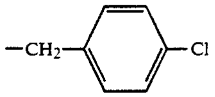 |
| 88 | 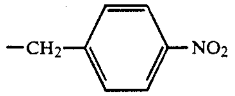 |
| 89 | 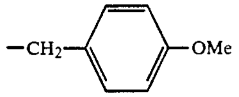 |
| 90 | 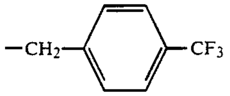 |
| 91 | 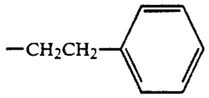 |
| 92 | $-CH_2CH=CH_2$ |
| 93 | 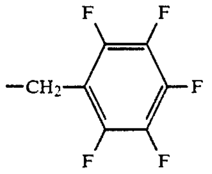 |
| 94 | 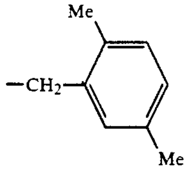 |
| 95 | 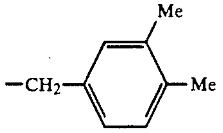 |
| 96 | 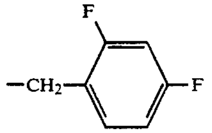 |
| 97 | 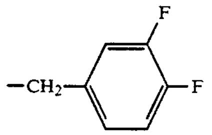 |

TABLE 7-continued

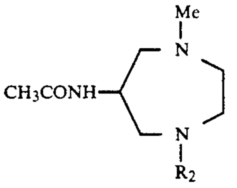

| Ex. | $R_2$ |
|---|---|
| 98 | 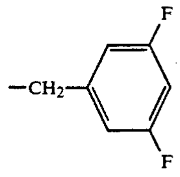 |
| 99 | $-CH_2CH_3$ |
| 100 | 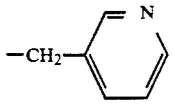 |
| 101 | 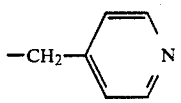 |
| 102 | 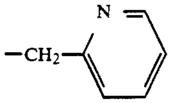 |
| 103 | 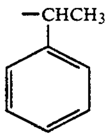 |
| 104 | 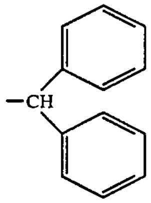 |

EXAMPLE 105

Preparation of 1,4-dimethyl-6-hydroxyhexahydro-1H-1,4-diazepine

A solution of 6-acetoxyhexahydro-1H-1,4-diazepine dihydrobromide (20 g) prepared according to the method of J. Org. Chem., 36, 1711 (1971), 35% formaldehyde (16.1 g) and formic acid (20 ml) is refluxed with stirring for 7 hours. The solvent is evaporated under reduced pressure, and the residue is diluted with cool water. The excess potassium carbonate is added to the aqueous solution, and the resulting solution is extracted with chloroform. The organic layer is dried over magnesium sulfate, and the solvent is evaporated under reduced pressure to give the title compound (11.5 g) as a pale yellow oil.

$^1$H-NMR spectrum ($CDCl_3$, δppm): 2.41 [(6H, s, 2(—NC$\underline{H}_3$)], 2.38–2.50 (2H, m), 2.66–2.84 (6H, m), 3.77 (1H, m, —CONHC$\underline{H}$—).

EXAMPLE 106

(1) To a mixture of tris(hydroxymethyl)nitromethane (118.9 g), sodium bicarbonate (40 g) and water (1000 ml), N-benzyl-N'-methylethylenediamine (123 g) is added, and the reaction mixture is heated at about 50° C. for 2 hours. After cooling, the solution is extracted with dichloromethane, and the organic layer is washed with saturated aqueous sodium chloride and dried over magnesium sulfate. The solvent is evaporated under reduced pressure to give 1-benzyl-6-hydroxymethyl-4-methyl-6-nitrohexahydro-1H-1,4-diazepine as an oil.

$^1$H-NMR spectrum ($CDCl_3$, δppm): 2.41 [(6H, s, 2(—NC$\underline{H}_3$)], 2.47–2.80 (4H, m), 2.91–3.51 (4H, m), 3.63, 3.73 (each 1H, each d, each J=12Hz, —C$\underline{H}_2$Ph), 3.80 (2H, s, —C$\underline{H}_2$OH).

(2) To a solution of 1-benzyl-6-hydroxymethyl-4-methyl-6-nitrohexahydro-1H-1,4-diazepine in methanol (800 ml), potassium tert-butoxide (97 g) is added, and the solution is heated at about 40° C. for 30 minutes. The solvent is evaporated under reduced pressure, and the residue is diluted in a solution of hydroxylamine hydrochloride (60 g) in water (500 ml) and extracted with dichloromethane. The organic layer is washed with saturated aqueous sodium chloride solution and dried over magnesium sulfate. The solvent is evaporated under reduced pressure, and the residue is chromatographed on silica gel with elution of ethyl acetate. Fractions containing the object compound are pooled and evaporated under reduced pressure to give 1-benzyl-4-methyl-6-nitrohexahydro-1H-1,4-diazepine (45 g) as a pale yellow oil.

$^1$H-NMR spectrum ($CDCl_3$, δppm): 2.44 (3H, s, —NC$\underline{H}_3$), 2.50–2.78 (4H, m), 3.10–3.45 (4H, m), 3.74 (2H, dd, J=15Hz, J=20Hz, —C$\underline{H}_2$Ph), 4.62 (1H, quint, —CONHC$\underline{H}$—)

(3) 1-Benzyl-4-methyl-6-nitrohexahydro-1H-1,4-diazepine (38 g) is dissolved in 95% ethanol (700 ml) and hydrogenated over Raney-nickel (about 5 g) at 25° C. After the calculated amount of the hydrogen is absorbed, the catalyst is filtered off. The filtrate is evaporated under reduced pressure to give a crude oil. The oil is dissolved in chloroform (200 ml), and acetic anhydride (30 g) is added to the solution. The reaction mixture is stirred at 25° C. for 2 hours, and water is added to the reaction mixture. The aqueous layer is separated and basified with sodium hydroxide solution, and extracted with chloroform. The organic layer is washed successively with water and saturated aqueous sodium chloride solution, and dried over magnesium sulfate The solvent is evaporated under reduced pressure, and the residue is chromatographed on silica gel with elution of chloroform-methanol (9:1). Fractions containing the object compound are pooled and evaporated under reduced pressure to give the title compound (49 g) in Example 72.

EXAMPLE 107

6-Acetylamino-1-benzyl-4-methylhexahydro-1H-1,4-diazepine (19.0 g) is dissolved in ethanol (300 ml) and acetic acid (30 ml) and hydrogenated over 10% palladium on carbon (3 g) at 25° C. After the calculated amount of the hydrogen is absorbed, the catalyst is filtered off. The filtrate is evaporated under reduced pressure to give an oil. 35% Formaldehyde (19.0 g) and formic acid (25 ml) is added to the oil, and the reaction mixture is refluxed with stirring for 7 hours. The solvent is evaporated under reduced pressure, and the residue is diluted with aqueous sodium hydroxide solution. Excess potassium carbonate is added to the solution, and the solution is extracted with chloroform. The organic solvent is dried over magnesium sulfate, and the solvent is evaporated under reduced pressure. The residue is chromatographed on silica gel with elution of chloroform-methanol (9:1). Fractions containing the object compound are pooled and evaporated under reduced pressure to give the title compound in Example 73.

EXAMPLE 108

Preparation of 6-amino-1-benzyl-2,4-dimethylhexahydro-1H-1,4-diazepine (1) To a solution of 2-benzylamino-1-propanol (113.9 g) in chloroform (700 ml), thionyl chloride (140 ml) is added dropwise at 0° C., and the mixture is refluxed for 8.5 hours. The solvent is evaporated under reduced pressure, and isopropyl alcohol (200 ml) is added in small portions to the residue at 0° C. The resulting precipitates are collected and washed successively with isopropyl alcohol and diethyl ether, and dried to give N-(β-chloropropyl)benzylamine hydrochloride (139.8 g).

(2) N-(β-Chloropropyl)benzylamine hydrochloride (50.0 g) is added in small portion to 30% monomethylamine ethanol solution (250 ml) at 0° C., and the reaction mixture is stirred at 50° C. for 20 hours. The solvent is evaporated under reduced pressure, and the residue is diluted in a solution of potassium hydroxide (34 g) in water (53 ml) and extracted with chloroform. The organic solvent is dried over magnesium sulfate and evaporated under reduced pressure to give an oil. $N^2$-Benzyl-$N^1$-methyl-1,2-propylenediamine (29.8 g) is obtained from the oil by vacuum distillation, b.p. 96°–97° C. (0.04 mmHg).

(3) To a solution of tris(hydroxymethyl)nitromethane (10.3 g), sodium bicarbonate (3 g), and water (100 ml), $N^2$-benzyl-$N^1$-methyl-1,2-propylenediamine (12 g) is added, and the reaction mixture is heated at about 50° C. for 2.5 hours. After cooling, the reaction mixture is extracted with dichloromethane, and the organic layer is washed with water and saturated aqueous sodium chloride and dried over magnesium sulfate. The solvent is evaporated under reduced pressure to give an oil. Potassium tert-butoxide (7.6 g) is added in small portions to the solution of the above oil in methanol (100 ml), and the solution is heated at about 30° C. for 30 minutes. The solvent is evaporated under reduced pressure, and the residue is diluted in a solution of 95% hydroxylamine hydrochloride (5.0 g) in water (50 ml) and extracted with dichloromethane. The organic layer is washed with saturated aqueous sodium chloride and dried over magnesium sulfate. The solvent is evaporated under reduced pressure, and the residue is chromatographed on silica gel with elution of ethyl acetate. Fractions containing the object compound are pooled and evaporated under reduced pressure to give 1-benzyl-2,4-dimethyl-6-nitrohexahydro-1H-1,4-diazepine (5.1 g) as a pale yellow oil.

(4) 1-Benzyl-2,4-dimethyl-6-nitrohexahydro-1H-1,4-diazepine (5.1 g) is dissolved in ethanol (100 ml) and acetic acid (5 ml) and hydrogenated over Raney-nickel (about 1 g) at 25° C. After the calculated amount of the hydrogen is absorbed, the catalyst is filtered off. The filtrate is evaporated under reduced pressure. The residue is dissolved in chloroform (100 ml), and acetic anhydride (4.0 g) is added to the solution. The reaction mixture is stirred for 2 hours at 25° C., diluted with aqueous sodium hydroxide solution, and extracted with chloroform. The organic layer is washed successively with water, aqueous sodium hydroxide solution, and saturated aqueous sodium chloride solution, and dried over magnesium sulfate. The solvent is evaporated under reduced pressure, the residue is chromatographed on silica gel with elution of chloroform-methanol (9:1). Fractions containing the object compound are pooled and evaporated under reduced pressure to give 6-acetylamino-1-benzyl-2,4-dimethylhexahydro-1H-1,4-diazepine (1.8 g) as an oil. The above compound is dissolved in 10% hydrochloric acid (20 ml) and is refluxed for 2 hours. After cooling, the reaction mixture is basified with aqueous sodium hydroxide solution and extracted with chloroform. The organic layer is washed successively with water and saturated aqueous sodium chloride solution, and dried over magnesium sulfate. The solvent is evaporated under reduced pressure to give the title compound (1.5 g).

EXAMPLE 109

Preparation of 6-amino-1-benzyl-3,4-dimethylhexahydro-1H-1,4-diazepine

The title compound is prepared in substantially the same manner as in Example 108, using 3-benzylamino-2-propanol in place of 2-benzylamino-1-propanol in Example 108.

EXAMPLE 110

Preparation of 6-benzensulfonylamino-1-benzyl-4-methylhexahydro-1H-1,4-diazepine A mixture of 1-benzenesulfonyl-2-bromomethylethylenimine (27.2 g), N-benzyl-N'-methylethylenediamine (16.2 g), triethylamine (19.9 g) and chloroform (350 ml) is refluxed with stirring for 5 hours. The solvent is evaporated under reduced pressure, and the residue is purified by silica gel chromatography to give the title compound (7.9 g) as an oil.

EXAMPLE 111

| | per 1,000 ampules |
|---|---|
| N-[1-(3-methylbenzyl)-4-methylhexahydro-1H-1,4-diazepin-6-yl]-1H-indazole-3-carboxamide dihydrochloride | 10 g |
| Citric acid | 10 g |
| Sorbitol | 50 g |
| Sodium hydroxide | q.s. |
| Water for injection | q.s. |
| | 2000 ml |

N-[1-(3-methylbenzyl)-4-methylhexahydro-1H-1,4-diazepin-6-yl]-1H-indazole-3-carboxamide dihydrochloride is dissolved in a sufficient amount of water for injection, and citric acid and sorbitol are added to the solution. After sodium hydroxide is added to the solution to adjust pH value to 4.5, water for injection is added to the solution to give total amount. The above solution is filtered by membrane filter (0.22 μm) and the filtrate is filled into 2 ml-ampules, and the ampules are sterilized at 121° C. for 20 minutes.

EXAMPLE 112

| | per 1,000 tablets |
|---|---|
| N-[1-(3-fluorobenzyl)-4-methylhexahydro-1H-1,4-diazepin-6-yl]-1H-indazole-3-carboxamide hemifumarate | 10 g |
| lactose | 76.5 g |
| Corn starch | 28 g |
| Microcrystalline cellulose | 25 g |
| Hydroxypropylcellulose | 3.5 g |
| Light anhydrous silicic acid | 0.7 g |
| Magnesium stearate | 1.3 g |

The above components are blended, granulated and made into 1,000 tablets each weighing 145 mg by a conventional method.

EXAMPLE 113

| | per 1,000 capsules |
|---|---|
| N-[1-(3-pyridylmethyl)-4-methylhexahydro-1H-1,4-diazepin-6-yl]-1H-indazole-3-carboxamide 5/2 fumarate | 10 g |
| lactose | 190 g |
| Corn starch | 22 g |
| Hydroxypropylcellulose | 3.5 g |
| Light anhydrous silicic acid | 1.8 g |
| Magnesium stearate | 2.7 g |

The above components are blended, granulated and filled into 1,000 capsules by a conventional method.

EXAMPLE 114

| | per 1,000 g |
|---|---|
| N-[1-(2-cyanobenzyl)-4-methylhexahydro-1H-1,4-diazepin-6-yl]-1H-indazole-3-carboxamide oxalate 1/4 hydrate | 20 g |
| lactose | 950 g |
| Hydroxypropylcellulose | 25 g |
| Light anhydrous silicic acid | 5 g |

The above components are blended and made into fine granule by a conventional method.

We claim:

1. A compound of the formula

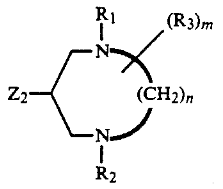

(III')

wherein $R_1$ and $R_2$ are identical or different and each represents (1) hydrogen, (2) a $C_1$–$C_6$ alkyl group, (3) a $C_1$–$C_6$ alkyl group substituted by (a) $C_3$–$C_8$ cycloalkyl, (b) $C_5$–$C_8$ cycloalkenyl, (c) $C_1$–$C_6$ alkoxy, (d) hydroxy,
(e) cyano,
(f) oxo,
(g) $C_2$–$C_4$ alkanoyloxy,
(h) an unsubstituted, mono- or di-substituted benzoyloxy group said substituent being halogen, $C_1$–$C_4$ alkyl, trifluoromethyl, hydroxy, $C_1$–$C_4$ alkoxy, amino, nitro, cyano or carboxy,
(i) amino,
(j) mono- or di-$C_1$–$C_4$ alkylamino,
(k) $C_2$–$C_4$ alkanoylamino,
(l) an unsubstituted, mono- or di-substituted benzoylamino group the substituent being halogen, $C_1$–$C_4$ alkyl, trifluoromethyl, hydroxy, $C_1$–$C_4$ alkoxy, amino, nitro, cyano or carboxy,
(m) a 5 or 6-membered monocyclo- or bicycloheteroaromatic group having 1 to 2 hetero atoms selected from oxygen and nitrogen, or
(n) halogen;
(4) a $C_3$–$C_8$ cycloalkyl group,
(5) a $C_2$–$C_6$ alkenyl group,
(6) a $C_5$–$C_8$ cycloalkenyl group,
(7) a $C_2$–$C_6$ alkynyl group,
(8) a phenyl-$C_1$–$C_6$ alkyl group in which the phenyl is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) mono- or di-$C_1$–$C_6$ alkylamino,
(h) $C_2$–$C_6$ alkanoylamino,
(i) an unsubstituted, mono- or di-substituted benzoylamino group the said substituent being halogen, $C_1$–$C_4$ alkyl, trifluoromethyl, hydroxy, $C_1$–$C_4$ alkoxy, amino, nitro, cyano or carboxy,
(j) nitro,
(k) cyano,
(l) carboxy or
(m) $C_2$–$C_4$ alkoxycarbonyl;
(9) a $C_2$–$C_6$ alkoxycarbonyl group,
(10 ) a phenyl-$C_1$–$C_6$ alkyloxycarbonyl group in which the phenyl is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) nitro,
(h) cyano or
(i) carboxy;
(11) a $C_2$–$C_6$ alkanoyl group, or
(12) a benzoyl group which is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) nitro,
(h) cyano or
(i) carboxy; or
$R_1$ and $R_2$, taken together, form a $C_1$–$C_6$ alkylene group;
$R_3$ represents
(1) a hydrogen atom,
(2) a $C_1$–$C_6$ alkyl group, or
(3) a phenyl group;
$Z_2$ represents —$NR_6R_7$ in which $R_6$ represents a hydrogen atom,
$R_7$ represents
(1) a hydrogen atom,
(2) a $C_2$–$C_6$ alkoxycarbonyl group,
(3) a phenyl-$C_1$–$C_6$ alkyloxycarbonyl group in which the phenyl is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) nitro,
(h) cyano or
(i) carboxy;
(4) a $C_2$–$C_6$ alkanoyl group,
(5) a benzoyl group which is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) nitro,
(h) cyano or
(i) carboxy;
(6) a $C_1$–$C_6$ alkylsulfonyl group,
(7) a phenylsulfonyl group which may optionally be substituted by
(a) halogen,
(b) $C_1$–$C_6$ alkyl,
(c) trifluoromethyl,
(d) hydroxy,
(e) $C_1$–$C_6$ alkoxy,
(f) amino,
(g) nitro,
(h) cyano or
(i) carboxy; or
(8) a trityl group; or
$R_6$ and $R_7$, together with the nitrogen atom to which they are bonded, may represent a phthalimide group,
m represents 1 or 2, and
n represents 2,
provided that $R_1$ and $R_2$ do not simultaneously represent a benzyl group.

2. A compound of claim 1 wherein
$R_2$ represents
(1) a hydrogen atom,
(2) a $C_1$–$C_6$ alkyl group,
(3) a $C_1$–$C_6$ alkyl group substituted by
(a) $C_3$–$C_8$ cycloalkyl,
(b) $C_5$–$C_8$ cycloalkenyl,
(c) $C_1$–$C_6$ alkoxy,
(d) hydroxy,
(e) oxo,
(f) a 5 or 6-membered monocyclo- or bicycloheteroaromatic group having 1 to 2 hetero atoms selected from oxygen and nitrogen, or
(g) halogen;
(4) a $C_3$–$C_8$ cycloalkyl group,
(5) a $C_2$–$C_6$ alkenyl group, (6) a $C_5$–$C_8$ cycloalkenyl group,
(7) a $C_2$–$C_6$ alkynyl group,
(8) a phenyl-$C_1$–$C_6$ alkyl group in which the phenyl is unsubstituted or is substituted by
(a) halogen,
(b) $C_1$–$C_6$ alkyl,
(c) trifluoromethyl,
(d) hydroxy,
(e) $C_1$–$C_6$ alkoxy,
(f) amino,
(g) mono- or di-$C_1$–$C_6$ alkylamino,
(h) $C_2$–$C_6$ alkanoylamino,
(i) benzoylamino,
(j) nitro,
(k) cyano,
(l) carboxy or
(m) $C_2$–$C_4$ alkoxycarbonyl;
(9) a $C_2$–$C_6$ alkoxycarbonyl group,
(10) a phenyl-$C_1$–$C_6$ alkoxycarbonyl group in which the phenyl is unsubstituted or is substituted by
(a) halogen,
(b) $C_1$–$C_6$ alkyl,
(c) trifluoromethyl or
(d) $C_1$–$C_6$ alkoxy;
(11) a $C_2$–$C_6$ alkanoyl group, or
(12) a benzoyl group which is unsubstituted or is substituted by
(a) halogen,
(b) $C_1$–$C_6$ alkyl,
(c) trifluoromethyl or
(d) $C_1$–$C_6$ alkoxy;
$R_3$ represents
(1) a hydrogen atom, or
(2) a $C_1$–$C_6$ alkyl group,
$Z_2$ represents —$NR_6R_7$ in which $R_6$ represents a hydrogen atom, and
$R_7$ represents
(1) a hydrogen atom,
(2) a $C_2$–$C_6$ alkoxycarbonyl group,
(3) a phenyl-$C_1$–$C_6$ alkyloxycarbonyl group in which the phenyl is unsubstituted or substituted by
(a) halogen,
(b) $C_1$–$C_6$ alkyl,
(c) trifluoromethyl or
(d) $C_1$–$C_6$ alkoxy;
(4) a $C_2$–$C_6$ alkanoyl group,
(5) a benzoyl group which is unsubstituted or is substituted by
(a) halogen,
(b) $C_1$–$C_6$ alkyl,
(c) trifluoromethyl or
(d) $C_1$–$C_6$ alkoxy;
(6) a $C_1$–$C_6$ alkylsulfonyl group,
(7) a phenylsulfonyl group which is unsubstituted or is substituted by
(a) halogen,
(b) $C_1$–$C_6$ alkyl,
(c) trifluoromethyl or
(d) $C_1$–$C_6$ alkoxy; or
(8) a trityl group; or
$R_6$ and $R_7$, together with the nitrogen atom to which they are bonded, may represent a phthalimide group.

3. The compound of claim 1 wherein $R_1$ represents a $C_1$–$C_6$ alkyl group.

4. The compound of claim 2 wherein
$R_2$ represents
a hydrogen atom,
a $C_1$–$C_6$ alkyl group,
a $C_1$–$C_6$ alkyl group substituted by
$C_3$–$C_6$ cycloalkyl,
$C_5$–$C_6$ cycloalkenyl, or
5 or 6 membered monocyclo- or bicyclo-heteroaromatic having 1 to 2 heteroatoms selected from oxygen and nitrogen atoms;
a $C_5$–$C_6$ cycloalkyl group,
an allyl group, or
a phenyl-$C_1$–$C_4$ alkyl group in which the phenyl is unsubstituted or is mono- or di-substituted by
halogen,
$C_1$–$C_4$ alkyl,
trifluoromethyl,
$C_1$–$C_4$ alkoxy,
nitro or
cyano; and
m represents a number of 1.

5. The compound of claim 4 wherein $R_1$ represents a $C_1$–$C_4$ alkyl group,
$R_2$ represents
a hydrogen atom,
a $C_1$–$C_4$ alkyl group,
a pyridylmethyl group, or
a benzyl group which is unsubstituted or is mono- or di-substituted by
halogen,
$C_1$–$C_4$ alkyl,
trifluoromethyl,
$C_1$–$C_4$ alkoxy or
cyano;
$R_3$ represents
a hydrogen atom, or
a $C_1$–$C_4$ alkyl group,
$Z_2$ represents —$NR_6R_7$ is which $R_6$ represents a hydrogen atom, and
$R_7$ represents
a hydrogen atom,
a $C_2$–$C_4$ alkoxycarbonyl group,
a benzyloxycarbonyl group which is unsubstituted or is mono- or di-substituted by
halogen,
$C_1$–$C_4$ alkyl,
trifluoromethyl, or
$C_1$–$C_4$ alkoxy;
a $C_2$–$C_4$ alkanoyl group,
a benzoyl group which is unsubstituted or is mono- or di-substituted by
halogen,
$C_1$–$C_4$ alkyl,
trifluoromethyl or
$C_1$–$C_4$ alkoxy;
a $C_1$–$C_4$ alkylsulfonyl group,
a phenylsulfonyl group which is unsubstituted or is mono-substituted by
halogen,
$C_1$–$C_4$ alkyl,
trifluoromethyl or
$C_1$–$C_4$ alkoxy; or
a trityl group; or
$R_6$ and $R_7$, together with the nitrogen atom to which they are bonded, may represent a phthalimide group.

6. The compound of claim 5 wherein $R_1$ represents a methyl group or an ethyl group,
$R_2$ represents
a hydrogen atom,
a methyl group, an ethyl group,
a pyridylmethyl group,
a benzyl group,
a methylbenzyl group,
a fluorobenzyl group,
a chlorobenzyl group,
a bromobenzyl group,
a trifluorobenzyl group,
a methoxybenzyl group,
a cyanobenzyl group,
a difluorobenzyl group, or
a dimethylbenzyl group,
$R_3$ represents a hydrogen atom, or a methyl group,
$Z_2$ represents —$NR_6R_7$ in which $R_6$ represents a hydrogen atom, and
$R_7$ represents
a hydrogen atom,
a methoxycarbonyl group,
a ethoxycarbonyl group,
a benzyloxycarbonyl group,
a methylbenzyloxycarbonyl group,
a methoxylbenzyloxycarbonyl group,
an acetyl group,
a propionyl group,
a benzoyl group,
a methylbenzoyl group,
a methoxybenzoyl group,
a methylsulfonyl group,
an ethylsulfonyl group,
a phenylsulfonyl group,
a methylphenylsulfonyl group, or
a trityl group, or
$R_6$ and $R_7$, together with the nitrogen atom to which they are bonded, may represent a phthalimide group.

7. A compound represented by the formula (III')

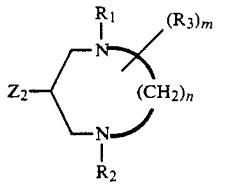

(III')

wherein
$R_1$ represents hydrogen or $C_1$-$C_6$ alkyl,
$R_2$ represents
(1) hydrogen;
(2) $C_1$-$C_6$ alkyl;
(3) $C_1$-$C_6$ alkyl substituted by (a) $C_3$-$C_6$ cycloalkyl, (b) $C_5$-$C_6$ cycloalkenyl, or (c) 5- or 6-membered monocyclo- or bicyclo-heteroaromatic having 1 or 2 hetero atoms selected from oxygen and nitrogen atoms;
(4) $C_5$-$C_6$ cycloalkyl;
(5) allyl; or
(6) phenyl-$C_1$-$C_4$ alkyl in which the phenyl is unsubstituted or is mono- or di-substituted by halogen, $C_1$-$C_4$ alkyl, trifluoromethyl, $C_1$-$C_4$ alkoxy, nitro or cyano,
$R_3$ represents hydrogen or $C_1$-$C_6$ alkyl,
$Z_2$ represents —$NR_6R_7$ in which $R_6$ represents hydrogen,
$R_7$ represents
(1) hydrogen;
(2) acetyl;
(3) ethoxycarbonyl;
(4) benzyloxycarbonyl;
(5) benzenesulfonyl; or
(6) 4-methylphenylsulfonyl; or
$R_6$ and $R_7$, together with the nitrogen atom to which they are bonded, may represent phthalimide,
m represents 1, and
n represents 2.

8. A compound of claim 7 in which $R_7$ represents hydrogen.

9. A compound of claim 7 in which $R_7$ represents acetyl.

10. A compound represented by the formula (III')

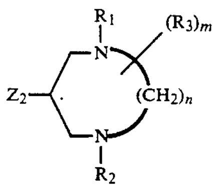

(III')

wherein
$R_1$ represents alkyl having 1 to 4 carbon atoms,
$R_2$ represents hydrogen, alkyl having 1 to 4 carbon atoms, pyridylmethyl; or benzyl which is unsubstituted or is mono- or di-substituted by halogen, $C_1$-$C_4$ alkyl, trifluoromethyl, $C_1$-$C_4$ alkoxy or cyano,
$R_3$ represents hydrogen or $C_1$-$C_4$ alkyl,
$Z_2$ represents —$NR_6R_7$ in which $R_6$ represents hydrogen,
$R_7$ represents
(1) hydrogen;
(2) acetyl;
(3) ethoxycarbonyl;
(4) benzyloxycarbonyl;
(5) benzenesulfonyl; or
(6) 4-methylphenylsulfonyl; or
$R_6$ and $R_7$, together with the nitrogen atom to which they are bonded, may represent phthalimide,
m represents 1, and
n represents 2.

11. A compound of claim 10 in which $R_7$ represents hydrogen.

12. A compound of claim 10 in which $R_7$ represents acetyl.

13. A compound of claim 10 in which $R_1$ represents methyl or ethyl,
$R_2$ represents methyl, ethyl, benzyl, methylbenzyl, fluorobenzyl, chlorobenzyl, bromobenzyl, trifluoromethylbenzyl, methoxybenzyl, cyanobenzyl, difluorobenzyl, dimethylbenzyl or pyridylmethyl,
$R_3$ represents hydrogen or methyl,
$Z_2$ represents —$NR_6R_7$ in which $R_6$ represents hydrogen, and
$R_7$ represents
(1) hydrogen;
(2) acetyl;
(3) ethoxycarbonyl;
(4) benzyloxycarbonyl;
(5) benzenesulfonyl; or
(6) 4-methylphenylsulfonyl; or
$R_6$ and $R_7$, together with the nitrogen atom to which they are bonded, may represent phthalimide.

14. A compound of claim 13 in which $R_7$ represents hydrogen.

15. A compound of claim 13 in which $R_7$ represents acetyl.

16. A compound selected from the group consisting of (1) 6-acetylamino-1-benzyl-4-methylhexahydro-1H-1,4-diazepine, (2) 6-acetylamino-1-(3-methylbenzyl)-4-methylhexahydro-1H-1,4-diazepine, (3) 6-acetylamino-1-(3-fluorobenzyl)-4-methylhexahydro-1H-1,4-diazepine, (4) 6-acetylamino-1-(4-cyanobenzyl)-4-methylhexahydro-1H-1,4-diazepine, (5) 6-acetylamino-1-(3-cyanobenzyl)-4-propylhexahydro-1H-1,4-diazepine, (6) 6-acetylamino-1-(3,5-difluorobenzyl)-4-methylhexahydro-1H-1,4-diazepine, (7) 6-acetylamino-1-(3-pyridylmethyl)-4-methylhexahydro-1H-1,4-diazepine, (8) 6-acetylamino-1,4-dimethylhexahydro-1H-1,4-diazepine, (9) 6-acetylamino-1,4-diethylhexahydro-1H-1,4-diazepine,

(10) 6-benzenesulfonylamino-1-benzyl-2,4-dimethylhexahydro-1H-1,4-diazepine,

(11) 6-benzyloxycarbonylamino-1-(3-methylbenzyl)-4-methylhexahydro-1H-1,4-diazepine,

(12) 6-ethoxycarbonylamino-1-benzyl-4-methylhexahydro-1H-1,4-diazepine,

(13) 6-(4-methylphenyl)sulfonylamino-1,4-dimethylhexahydro-1H-1,4-diazepine, and

(14) N-(1-benzyl-4-methylhexahydro-1H-1,4-diazepine-6-yl)-phthalimide.

* * * * *